United States Patent
Schu et al.

(10) Patent No.: US 6,438,422 B1
(45) Date of Patent: Aug. 20, 2002

(54) POWER DISSIPATION REDUCTION IN MEDICAL DEVICES USING ADIABATIC LOGIC

(75) Inventors: Carl A. Schu, Plymouth; Daniel R. Greeninger, Coon Rapids; David L. Thompson, Fridley, all of MN (US)

(73) Assignee: Medtronic, Inc., Minneapolis, MN (US)

(*) Notice: Subject to any disclaimer, the term of this patent is extended or adjusted under 35 U.S.C. 154(b) by 0 days.

(21) Appl. No.: 09/467,288

(22) Filed: Dec. 20, 1999

Related U.S. Application Data

(63) Continuation-in-part of application No. 09/181,460, filed on Oct. 28, 1998, now Pat. No. 6,023,641.

(51) Int. Cl.[7] .............................................. A61N 1/362
(52) U.S. Cl. .................................................. 607/16
(58) Field of Search .............................. 607/1, 2, 4, 5, 607/9, 16

(56) References Cited

U.S. PATENT DOCUMENTS

| | | | |
|---|---|---|---|
| 5,350,407 A | * 9/1994 | McClure et al. ............... | 607/16 |
| 5,473,269 A | 12/1995 | Dickson | |
| 5,473,526 A | 12/1995 | Svensson et al. | |
| 5,506,520 A | 4/1996 | Frank et al. | |
| 5,559,478 A | 9/1996 | Athas et al. | |
| 5,986,476 A | 11/1999 | De | |
| 5,999,849 A | 12/1999 | Gore et al. | |

OTHER PUBLICATIONS

Svensson et al., "Driving a capacitive load without dissipating fCV², " 1994 IEEE, Proc of the International Symposium on Low-Power Electronics and Design, San Diego, CA, Oct. 10–12, 1994.

Gail Robinson, "New design approach recycles electrons to save power—Clock-powered circuits set efficiency record," Electronic Times, 1997, n 983, p. 37.

Athas et al., "Energy-Recovery CMOS for Highly Pipelined DSP Designs," USC/Information Sciences Institute; IEEE, Proc. of the International Symposium on Low-Power electronics and Design, Monterey, CA, Aug. 12–14, 1996.

Chandrakasan et al., "Low Power Digital CMOS Design," Kluwer Academic Publishers, 1995, Third Printing 1998, pp. 181–218.

(List continued on next page.)

Primary Examiner—George R. Evanisko
(74) Attorney, Agent, or Firm—Girma Wolde-Michael

(57) ABSTRACT

A system for minimizing power dissipation within an implantable medical device through use of adiabatic logic is disclosed. The system includes a first and a second subcircuit of the implantable medical device. An electrical connection interconnects the first and the second subcircuits, the electrical connection including a capacitive element. Circuitry, which charges the capacitive element of the electrical connection to generate a ramp logic signal, is connected to the capacitive element. The ramp logic signal includes a frequency of less than 500 kilohertz, thereby creating a low frequency, low power system which reduces energy dissipation to the surrounding environment.

7 Claims, 20 Drawing Sheets

OTHER PUBLICATIONS

Athas et al., "Low–Power Digital Systems Based on Adiabatic–Switching Principles," IEEE Transactions of VLSI Systems, pp. 398–407, Dec. 1994.

Athas et al., "An Energy–Efficient CMOS Line Driver Using Adiabatic Switching," IEEE, Proc. of the Fourth Great Lakes Symposium on VLSI Design, pp. 159–164, Mar. 1994.

Lars Svensson, "AC–1: A Clock–Powered Microprocessor," Enterprise Integration Systems Division, USC/Information Sciences Institute, Aug. 20, 1997.

Tzartzanis et al., "Clock–Powered Logic for a 50 MHz Low–Power RISC Datapath," Information Sciences Institute, The Univ. of Southern California, Feb. 8, 1997.

Tzartzanis et al., "Retractile Clock–Powered Logic," Information Sciences Institute, Univ. of Southern California, Aug. 16, 1999.

Tzartzanis et al., "Clock–Powered CMOS: A Hybrid Adiabatic Logic Style for Energy–Efficient Computing," Information Sciences Institute, Univ. of Southern California, Mar. 22, 1999.

Athas et al., "AC–1: A Clock–Powered Microprocessor," 1997 IEEE, Proc. of the International Symposium on Low–Power Electronics and Design, Monterey, CA, Aug. 18–20, 1997.

Tzartzanis et al., "Clock–Powered Logic for a 50 MHz Low–Power RISC Datapath," 1997 IEEE, Digest of Technical Paperes of the International Solid–State Circuits Conference, San Francisco, CA, Feb. 6–8, 1997.

* cited by examiner

POWER DISSIPATION REDUCTION IN MEDICAL DEVICES USING ADIABATIC LOGIC

CROSS-REFERENCE TO RELATED APPLICATION

This application is a Continuation-In-Part application (CIP). This application is based upon and claims priority from U.S. patent application Ser. No. 09/181,460 for "Power Consumption Reduction in Medical Devices Employing Multiple Digital Signal Processors," to Thompson, filed Oct. 28, 1998 now U.S. Pat. No. 6,023,641, hereby incorporated by reference in its entirety.

THE FIELD OF THE INVENTION

The present invention relates to power consumption of integrated circuit designs such as circuits used in medical devices, particularly implantable devices. More particularly, the present invention relates to utilizing adiabatic logic designs to minimize power dissipation in an implantable medical device.

BACKGROUND OF THE INVENTION

Various devices require operation with low power consumption. For example, hand-held communication devices require such low power consumption and, in particular, implantable medical devices require low power capabilities. Implantable medical devices, for example, microprocessor-based implantable cardiac devices, such as implantable pacemakers and defibrillators, are required to operate with a lower power consumption to increase battery life and device longevity.

Generally, such low power devices are designed using complementary metal oxide semiconductor (CMOS) technology. CMOS technology is generally used because such technology has the characteristic of substantially zero "static" power consumption.

The power consumption of CMOS circuits consists generally of two power consumption factors, namely "dynamic" power consumption and "static" power consumption. Static power consumption is due to current leakage as the quiescent current of such circuits is zero. Dynamic power consumption is the dominant factor of power consumption for CMOS technology. Dynamic power consumption is basically due to the current required to charge internal and load capacitances during switching, i.e., the charging and discharging of such capacitances. The dynamic power (P) is equal to: $CV_{DD}^2F$, where C is the nodal capacitance, F is the clock or switching frequency, and $V_{DD}$ is the supply voltage for the CMOS circuit. As can be seen from the formula for calculating dynamic power (P), such dynamic power consumption of CMOS circuits is proportional to the square of the supply voltage ($V_{DD}$). In addition, the dynamic power (P) is proportional to the nodal capacitance (C) and the switching or clock frequency (F).

In accordance with the formula for dynamic power consumption, it is effective conventionally in CMOS integrated circuit designs to scale down the supply voltage for an entire device (e.g., hybrid) or integrated circuit (IC), i.e., operate the circuit at low supply voltages, to reduce power consumption for such designs. For example, in the Medtronic Spectrax®, circa 1979, IC circuitry is powered by one LiI cell versus two cells. This reduced the supply voltage to 2.8 volts from 5.6 volts, thus reducing overhead current. Voltages required to be greater than 2.8 volts are generated by a voltage doubler, or alternatively by a charge pump (e.g., output pacing pulses). Further, for example, in the Medtronic Symbios®, circa 1983, the logic circuitry is powered by a voltage regulator controlling the IC supply voltage to a "sum of thresholds" supply. This regulator provides a supply to the IC (i.e., $V_{DD}$) of several hundred millivolts above the sum of the n-channel and p-channel thresholds of the CMOS transistors making up the IC. This regulator is self-calibrating regarding manufacturing variations of the transistor thresholds.

Other devices reduce power consumption in other varied manners. For example, various device designs shutdown analog blocks and/or shut-off clocks to logic blocks not used at particular times, thereby reducing power. Further, for example, microprocessor-based devices historically use a "burst clock" design to operate a microprocessor at a very high clock rate (e.g., generally 500–1000 Kilohertz (kHz)), for relatively short periods of time to gain the benefit of a "duty cycle" to reduce average current drain. A much lower frequency clock (e.g., generally 32 kHz) is used for other circuitry and/or the processor when not in the high clock rate mode, i.e., burst clock mode. Many known processor-based implanted devices utilize the burst clock technique. For example, implanted devices available from Medtronic, Vitatron, Biotronic, ELA, Intermedics, Pacesetters, InControl, Cordis, CPI, etc., utilize burst clock techniques. A few illustrative examples which describe the use of a burst clock are provided in U.S. Pat. No. 4,561,442 to Vollmann et al., entitled "Implantable Cardiac Pacer With Discontinuous Microprocessor Programmable Anti Tachycardia Mechanisms and Patient Data Telemetry," issued Dec. 31, 1985; U.S. Pat. No. 5,022,395 to Russie, entitled "Implantable Cardiac Device With Dual Clock Control of Microprocessor," issued Jun. 11, 1991; U.S. Pat. No. 5,388,578 to Yomtov et al., entitled "Improved Electrode System For Use With An Implantable Cardiac Patient Monitor," issued Feb. 14, 1995; and U.S. Pat. No. 5,154,170 to Bennett et al., entitled "Optimization for Rate Responsive Cardiac Pacemaker," issued Oct. 13, 1992.

FIG. 1 represents a graphical illustration of energy/delay versus supply voltage for CMOS circuits such as a CMOS inverter 10 shown in FIG. 2 for illustrative purposes. The inverter 10 is provided with a supply voltage, $V_{DD}$, which is connected to the source of a PMOS field effect transistor (FET) 12. PMOS FET 12 has its drain connected to the drain of an NMOS FET 14 whose source is connected to ground. In this configuration, an input $V_i$ applied to both the gates of FETs 12, 14 is inverted to provide output $V_o$. Simply stated, with each clock cycle or logic level change, the input $V_i$ is inverted and produces output $V_o$.

As shown in FIG. 1, the circuit logic delay increases drastically as the supply voltage is reduced to near one volt, as represented by delay line 16 and energy/delay line 18. As such, reducing of the supply voltage ($V_{DD}$) continuously to lower levels is impractical because of the need for higher supply voltages when higher frequency operation is required. For example, generally CMOS logic circuits must periodically provide functionality at a higher frequency, e.g., burst clock frequency. However, as the supply voltage ($V_{DD}$) is decreased, such energy consumption is reduced by the square of the supply voltage ($V_{DD}$) as is shown by energy consumption line 20. Therefore, speed requires a higher supply voltage ($V_{DD}$) which is in direct conflict with low power consumption.

Other problems are also evident when lower supply voltages ($V_{DD}$) are used for CMOS circuit designs. When a lower supply voltage is selected, static leakage current losses may arise, particularly at lower frequencies, due to increased static leakage current losses.

Various techniques for reducing power consumption in devices are known in the art, some examples of which may be found in the references listed in Table 1 below.

TABLE 1

| Patent No. | Inventor | Issue Date |
|---|---|---|
| 4,031,899 | Renirie | 28 June 1977 |
| 4,460,835 | Masuoka | 17 July 1984 |
| 4,561,442 | Vollmann et al | 31 December 1985 |
| 4,791,318 | Lewis et al. | 13 December 1988 |
| 5,022,395 | Russie | 11 June 1991 |
| 5,154,170 | Bennett et al. | 13 October, 1992 |
| 5,185,535 | Farb et al. | 09 February 1993 |
| 5,388,578 | Yomtov et al. | 14 February 1995 |
| 5,610,083 | Chan et al. | 11 March 1997 |

All references listed in Table 1 herein above are hereby incorporated by reference in their respective entireties. As those of ordinary skill in the art will appreciate readily upon reading the Summary of the Invention, Detailed Description of the Embodiments, and claims set forth below, many of the devices and methods disclosed in the references of Table 1 and others incorporated by reference herein may be modified advantageously by using the teachings of the present invention.

SUMMARY OF THE INVENTION

Various embodiments of the present invention provide solutions to one or more problems existing in the prior art with respect to circuitry designs having power dissipation, particularly with respect to implantable medical devices. These problems include: (a) transistor circuits, including CMOS circuits, having a large power consumption which reduces battery life; (b) the inability to minimize power dissipation associated with interconnections of various elements or circuits; utilize low voltage supply levels effectively; (c) the inability to provide adequate processing capabilities such as high processing capabilities including telemetry uplink/downlink, morphology detection, initialization of devices, while still providing low processing capabilities such as sensing intrinsic beats, pacing, and low speed telemetry, with the desired power consumption; and (d) the inability to provide circuit designs that operate at lower frequencies and thus lower power consumption as opposed to the use of higher speed clocks such as burst clocks.

In comparison to known techniques for reducing power consumption in circuit designs, various embodiments of the present invention may provide one or more of the following advantages: (a) reduced power consumption through the use of adiabatic logic; (b) reduced power consumption due to a decreased lock frequency for circuit designs; (c) increased longevity of circuits, particularly implantable device circuitry; (d) reduced product size and minimization of static leakage current losses, i.e., static power consumption; and (e) multi-processor designs, DSP designs, and high performance processing designs with additional features/function opportunities due to the ability to reduce power dissipation associated with chip-to-chip and intrachip data and/or address bus signals.

Some embodiments of the invention include one or more of the following features: (a) an adiabatic logic design producing a ramp logic signal which minimizes power consumption; (b) circuitry designs which utilize an internal capacitance of a data and/or address bus interconnecting two chips or interconnecting two sub-components of a single chip; (c) a low frequency circuit design which minimizes power dissipation while providing a logic signal to various components or circuits of an implantable medical device; and (d) a resident design circuit which utilizes a resistor, inductor, capacitor configuration to minimize power dissipation to a component or circuit of an implantable medical device.

DESCRIPTION OF THE PREFERRED EMBODIMENTS

The present invention shall first generally be described with reference to FIGS. 3–7. Thereafter, the present invention shall be described with reference to illustrative configurations of implantable medical devices shown in FIGS. 8–20.

Figure 1:
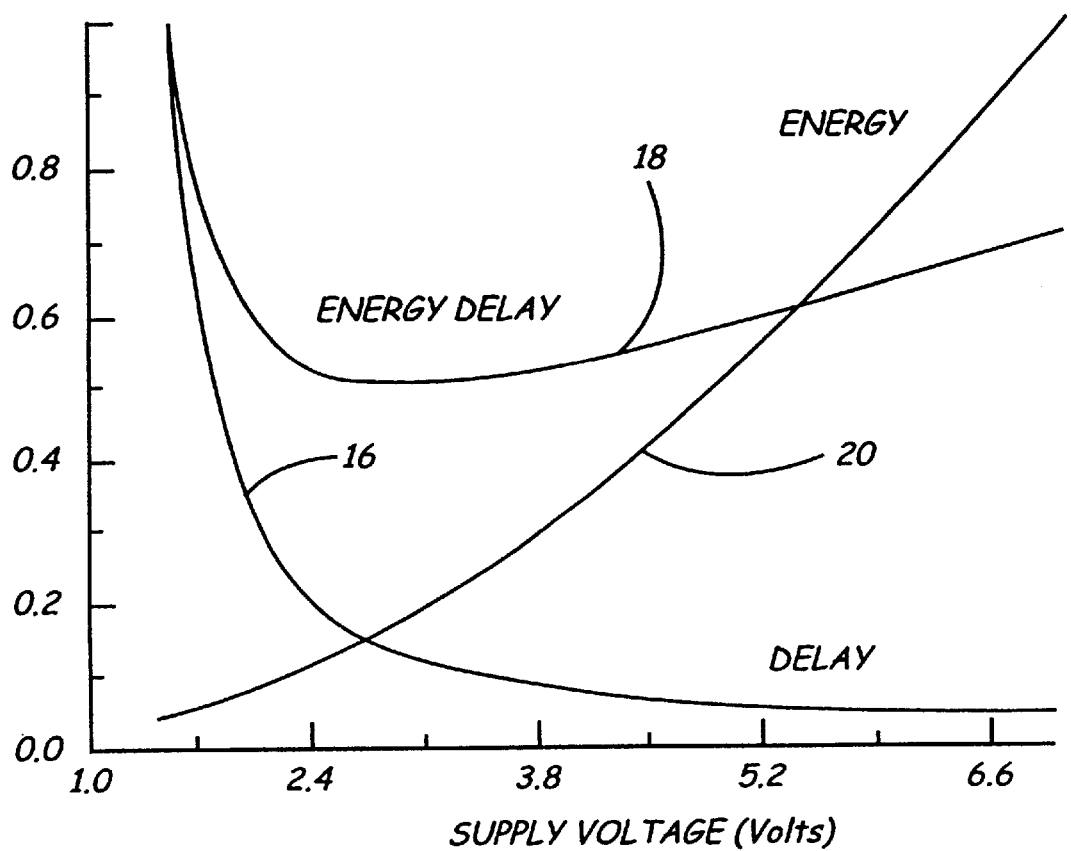
FIG. 1 is a graphical illustration showing energy/delay versus supply voltage for CMOS circuit operation.
Figure 2:
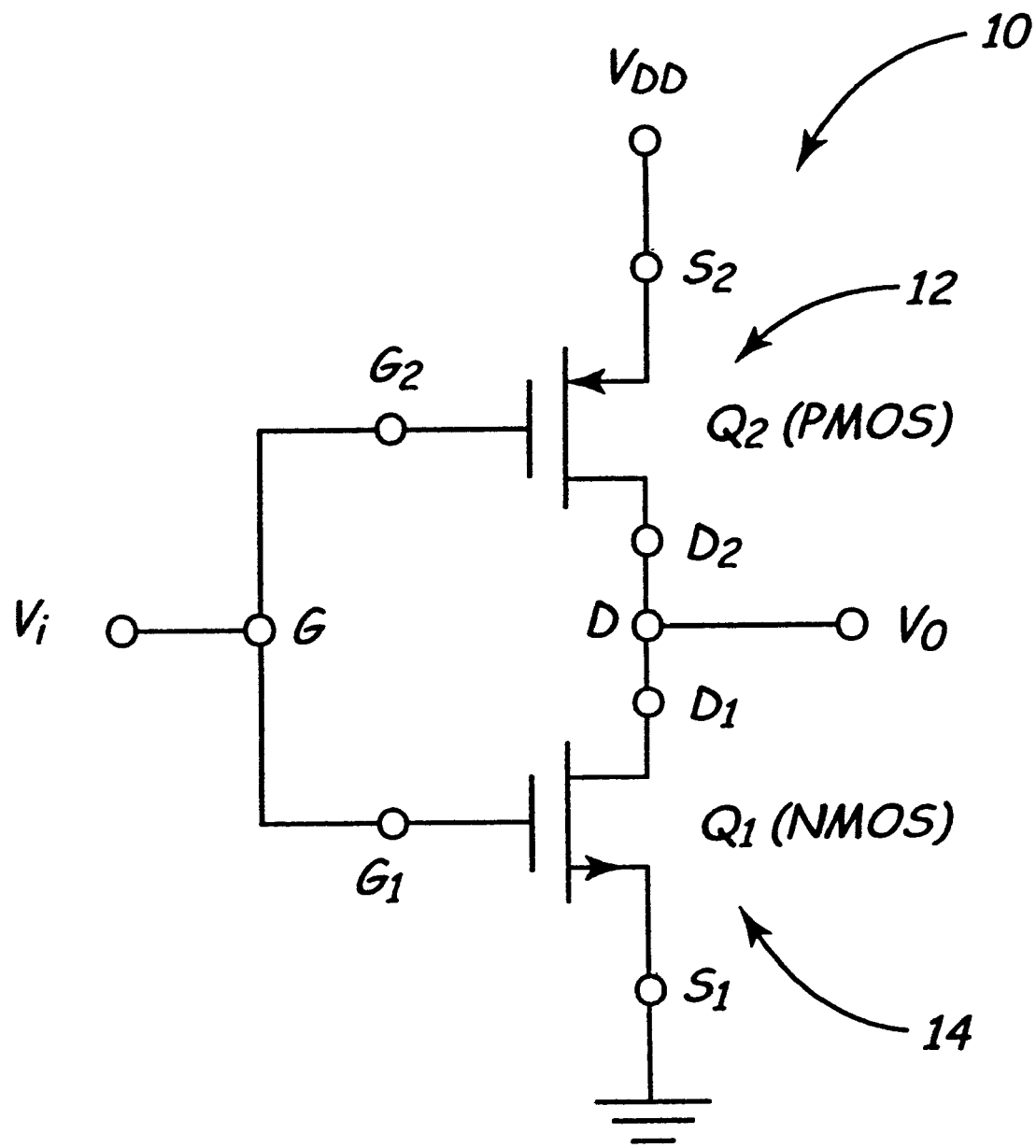
FIG. 2 shows a prior art CMOS inverter that is used as a building block in many CMOS circuit designs.
Figure 3:
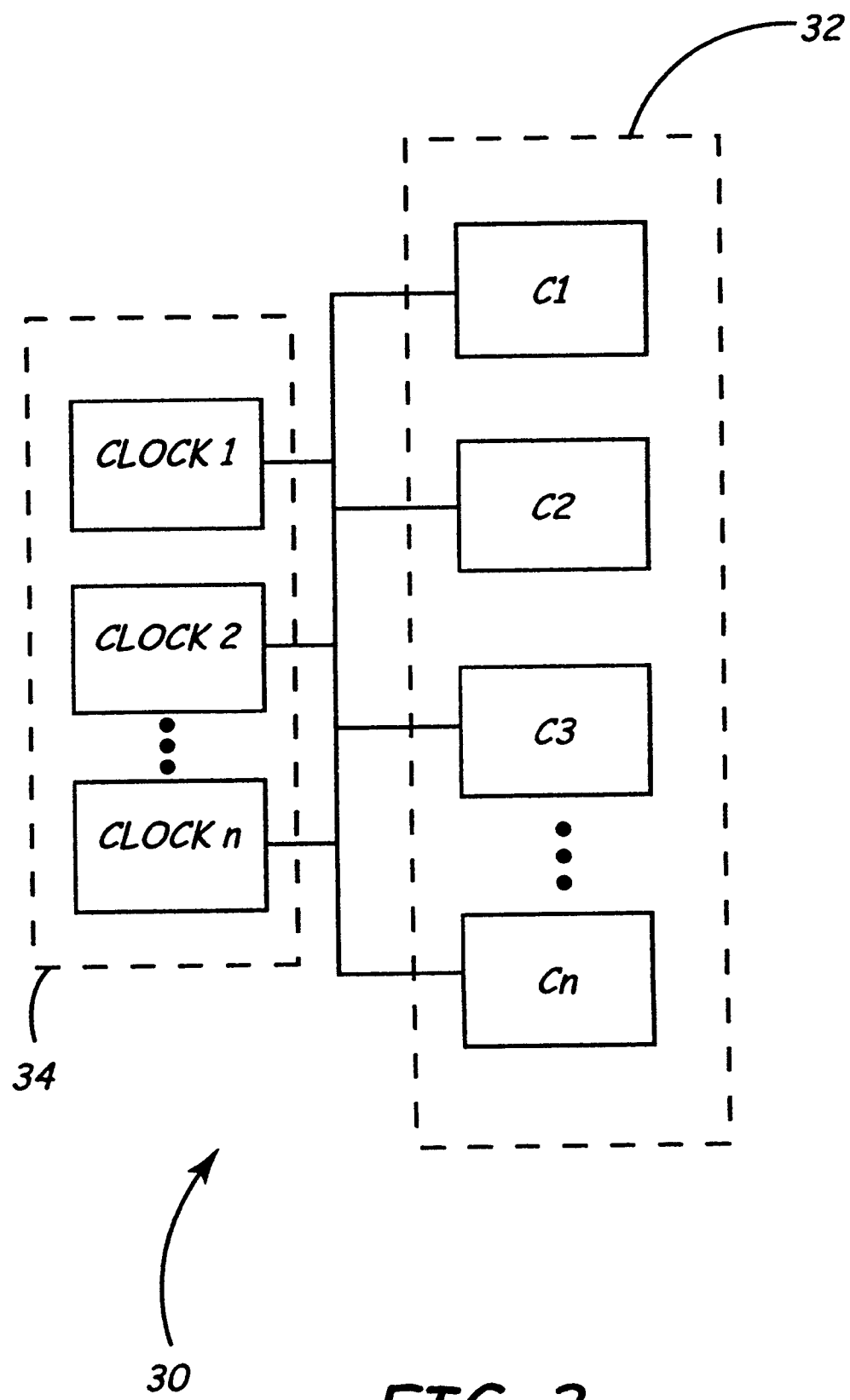
FIG. 3 is a block diagram of a just-in-time clocking system according to the present invention.

FIG. 3 shows a general block diagram of a just-in-time clock system 30. The just-in-time clock system 30 includes an integrated circuit 32 and a clock source 34. The integrated circuit 32 includes a plurality of circuits C1–Cn. Each circuit when operable is capable of performing one or more circuit functions. A function is defined as any operation performed on one or more inputs in a plurality of cycles resulting in an output. Generally, the functions performed by the various circuits C1–Cn are performed in a predetermined number of clock cycles. Clock source 34 is operable for providing clock signals at a plurality of clock frequencies generally shown as clock1—clockn.

The circuits C1–Cn of integrated circuit 32 may include discrete function circuits (i.e., logic circuits for operating upon one or more inputs to implement a particular function to provide one or more outputs therefrom), such as circuits operating on one input from a sensor to provide a representative signal to further functional circuitry, transceiver circuitry, conversion circuitry, etc. Further, the circuits C1–Cn may be data processing circuitry capable of performing multiple functions under program control or such circuits C1–Cn may implement firmware (software) functions/ routines that must complete prior to some succeeding event or prior to the start of the next function. For example, as described further herein with respect to illustrative embodiments of implantable medical devices, such circuits may include digital signal processing circuits, circuitry used for telemetry uplink/downlink, morphology detection circuitry, arrhythmia detection circuitry, monitoring circuitry, pacing circuitry, microprocessors, etc.

The functions performed by each of the circuits C1–Cn are typically required to be completed in a particular time period prior to a next functional process being undertaken. For example, one logic circuit may perform a function in a predetermined time period to provide an output required by another circuit, or for example, a function may need to be performed by processing circuitry during a particular period of time due to the need for other processing to be performed by such processing circuitry. For example, in an implantable medical device, processing to complete a particular function may need to be performed in a portion of a particular time interval such as a blanking interval, an upper rate interval, an escape interval, or refractory interval of a cardiac cycle, or further, such as during a pulse generator/ programmer handshake.

Clock source 34 may be configured in any manner for providing clock signals at a plurality of frequencies. Such a clock source may include any number of clock circuits wherein each provides a single clock signal at a particular frequency, the clock source 34 may include one or more adjustable clock circuits for providing clock signals over a continuous range of clock frequencies, and/or the clock source 34 may include a clock circuit that is operable to provide clock signals at discrete clock frequencies as opposed to over a continuous range. For example, the clock source 34 may include oscillators, clock dividers, timers, clock control circuitry or any other circuit elements required for providing clock signaling according to the present invention. Preferably, the clock source 34 is configured as a continuously oscillating low frequency clock and a controllable on/off higher frequency clock.

Figure 4A:
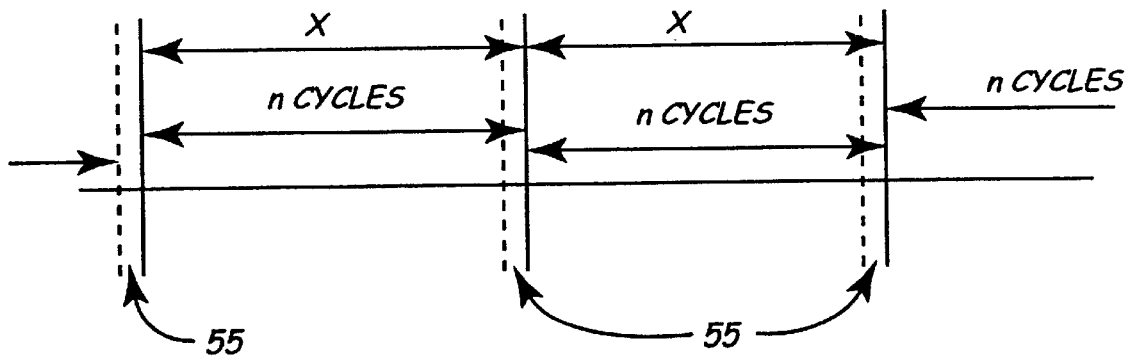
FIGS. 4A–4C show timing illustrations for use in describing the just-in-time clocking system of FIG. 3.
Figure 4B:
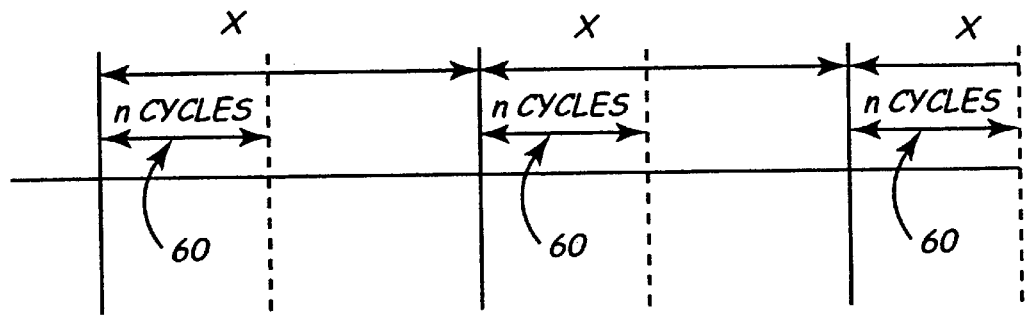

Just-in-time controllable clock operation of the just-in-time clocking system 30 of FIG. 3 shall be described with reference to FIGS. 4A–4C. As shown in FIG. 4A, time period (x) represents the time period in which a circuit, e.g., one of circuits C1–Cn, is required to complete one or more functions. The same time period (x) is shown in FIG. 4B. The time period x may be equated to any number of different time periods. For example, the time period may be the amount of time a processing circuit has to perform a particular detection function due to the need for a detection output by a certain point in time, may be a time period required to complete a particular function by a certain logic circuit so as to provide a timely output to a digital signal processing circuit, may be a time period to complete a firmware (software) routine, etc. Further, for example, the time period x may correspond to a cardiac cycle or a part thereof.

As shown in FIG. 4B, according to conventional processing, circuit functions were typically performed at a burst cycle frequency and, as such, the function performed required a time period 60. Therefore, only a small amount of time (i.e., time period 60) of the entire time period x was used to perform the one or more functions requiring n cycles of time to complete. In such a case, conventionally, such burst clocks were at a substantially high clock rate, e.g., 500–1000 kHz, for such short periods of time to gain the benefit of a "duty cycle" to reduce average current drain. However, such high clock rates may not be required for carrying out such functions, or all functions.

With just-in-time clocking according to the present invention, as shown in FIG. 4A, substantially the entire time period x is used to perform the one or more functions, which are completed in n cycles. In other words, the clock frequency, e.g., one of clock1--clockn, for the circuit performing the one or more functions during the time period x is set such that the one or more functions are completed in the maximum time available for performing such functions, i.e., the clock frequency is at its lowest possible value. In other words, a lower frequency clock is used such that the one or more functions are performed just-in-time for other circuit or routine functionality to be performed. In such a just-in-time manner, the clock frequency used to control the performance of such functions by the particular CMOS circuitry is lowered resulting in reduced power consumption by the CMOS circuitry, e.g., according to the calculations of dynamic power, the lower frequency results in proportional power reduction. With the lowering of the clock frequency, the integrated circuit 32 including the various circuits C1–Cn can be designed to operate at a lower frequency, e.g., as opposed to burst frequency, and also at various other frequencies depending upon need.

Preferably, as used herein, use of the substantially entire predetermined period of time may result in a completion of the one or more functions being performed prior to the end of the time period x as is represented by remainder time periods 55 in FIG. 4A. This remainder time period 55, for example, is preferably near 0 seconds.

Figure 4C:
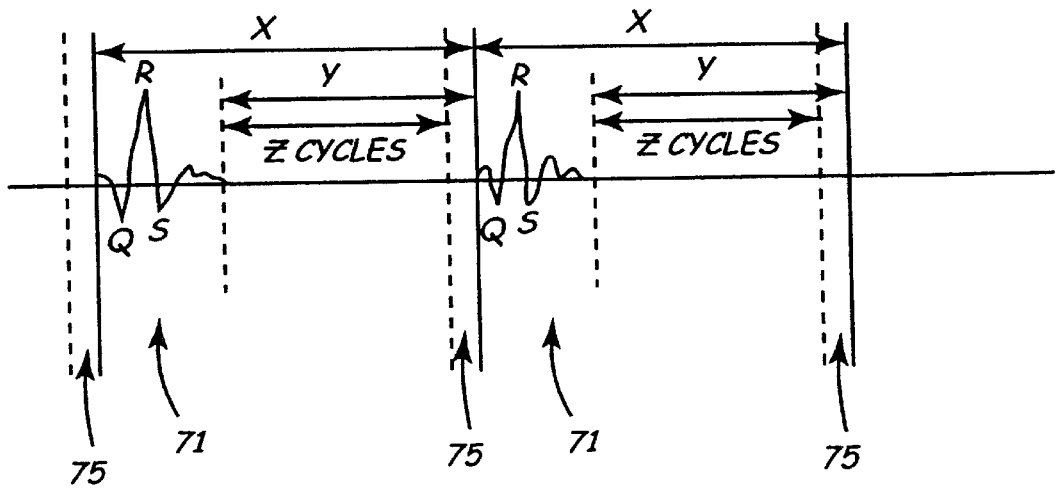

FIG. 4C shows an illustrative timing example for processing circuitry, which performs multiple functions. For example, the cardiac cycle of a patient is represented in FIG. 4C as time period x. During time period 71, i.e., during a QRS complex of the cardiac cycle, high speed processing is performed at a high clock frequency relative to a lower clock frequency used to control operation of the processing circuitry during time period y. During the time period y, when the processing circuitry is operated at a lower clock frequency, such lower clock frequency may be set such that the functions performed during z cycles are performed in substantially the entire maximum time period available for such processing, i.e., time period y. Once again, a small remainder time period 75 of the cardiac cycle time period x may exist. Such time period may be, for example, in the range of about 1.0 millisecond to about 10.0 milliseconds when the cardiac cycle is in the range of about 400 milliseconds to about 1200 milliseconds.

Figure 5:
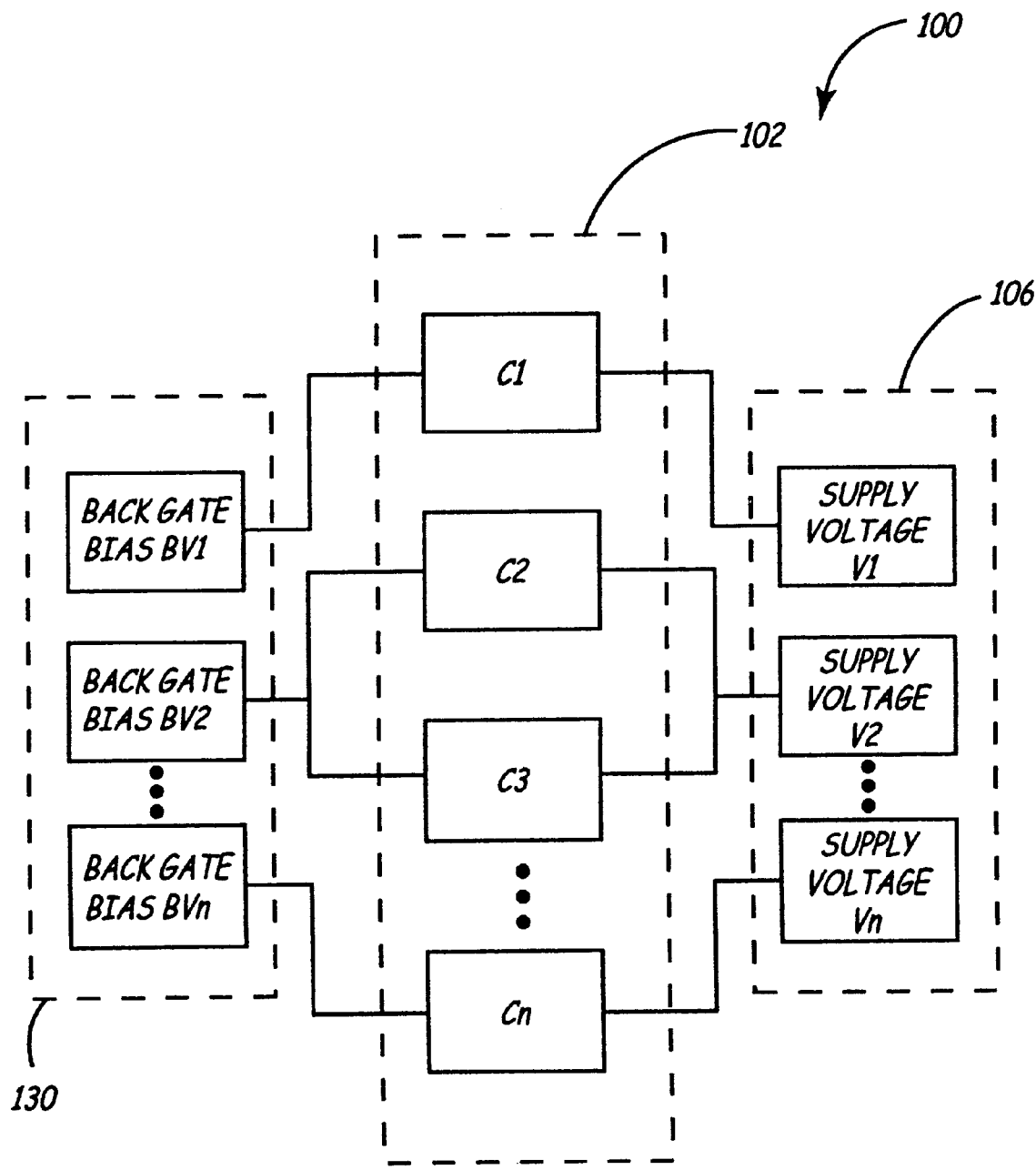
FIG. 5 is a block diagram illustration of a multiple supply voltage system according to the present invention.

FIG. 5 shows a general block diagram of a multiple supply voltage system 100 wherein one or more supply voltages are available and tailored for application to various circuits in an IC. The multiple supply voltage system 100 includes integrated circuit 102 and supply voltage source 106. Integrated circuit 102 includes circuits C1–Cn. Supply voltage source 106 is operable for providing a plurality of supply voltages V1–Vn. Each supply voltage from supply voltage source 106 is tailored to be applied to one or more circuits of circuits C1–Cn. As illustrated, supply voltage V1 is applied to circuit C1, supply voltage V2 is applied to circuit C2 and C3, and so forth.

The tailoring of the supply voltages V1–Vn to the particular circuits C1–Cn is dependent upon the frequency at which the circuits C1–Cn are required to be operated. For example, and as previously described, the logic delay of such CMOS circuits C1–Cn increases drastically as the supply voltage is reduced to near 1 volt. If such logic delay is tolerable, the supply voltage provided to a particular circuit will drastically reduce the power consumption for that particular circuit as the energy is reduced in proportion to the square of the supply voltage ($V_{DD}$). However, if such logic delay is not tolerable, for example, if the logic circuit performs a function that must be completed within a particular period of time, the reduction of the supply voltage ($V_{DD}$) applied to such a circuit will be limited depending upon the acceptable logic delay. However, the supply voltage $V_{DD}$ for any particular circuit can be reduced as low as possible yet meet adequate speed requirements.

The integrated circuit 102 may include various different circuits C1–Cn like those described with reference to FIG. 3. The supply voltage source 106 may be implemented using a variety of components and may include any number of voltage sources wherein each provides a single supply voltage level, may include one or more adjustable voltage sources for providing supply voltage levels over a continuous range of levels, and/or may include a voltage source that is operable to provide discrete supply voltage levels as opposed to levels over a continuous range. The supply voltage source may include a voltage divider, a voltage regulator, a charge pump, or any other elements for providing the supply voltages V1–Vn. Preferably, the supply voltage source 106 is configured as a charge pump.

Conventionally, the supply voltage ($V_{DD}$) is generally in the range of about 3 volts to about 6 volts. Preferably, in accordance with the present invention, the supply voltages V1–Vn are in the range of about 1 volt to about 3 volts dependant upon the CMOS technology used.

With reduction in supply voltage ($V_{DD}$), the threshold voltage ($V_T$) for the circuits is also reduced. For example, with supply voltages in the range of about 3 to about 6 volts, the threshold voltage for CMOS devices is generally in the range of about 0.8 volts to about 1.0 volt. Preferably, in implantable medical devices, lithium chemistries are utilized for implantable batteries. Such lithium chemistries are generally in the range of about 2.8 volts to about 3.3 volts and generally the CMOS circuitry has an associated threshold voltage of about 0.75. By reducing the supply voltages below 2.8, the voltage thresholds for CMOS devices may be decreased to as low as about 0.2 volts to about 0.3 volts.

Currently, there are various ultra low power logic designs operating at a supply voltage as low as about 1.1, e.g., such as logic designs for microprocessors for a laptop and other portable product designs. By utilizing the tailored supply voltages V1–Vn, low power or ultra low power logic designs may be used for at least some of the various circuits C1–Cn of integrated circuit 102. Other circuits may require supply voltages of a higher nature. With use of lower threshold levels due to lower supply voltages, static power consumption losses undesirably increase by several orders of magnitude.

Therefore, multiple supply voltage system 100 may further optionally include back gate bias source 130 for providing back gate bias voltages BV1–BVn to circuits C1–Cn of integrated circuit 102. Generally, the back gate bias voltages BV1–BVn are dependent upon the supply voltage V1–Vn applied to the circuits C1–Cn to adjust the threshold voltages for devices of circuits C1–Cn. For example, the threshold voltage ($V_T$) for the CMOS devices of the circuit may be at a lower value by providing a back gate bias voltage to the particular circuits supplied with the lower supply voltage. Further, for example, if circuit C1 is supplied with a lower supply voltage V1, then a back gate bias voltage BV1 may optionally be applied to circuit C1 to adjust the threshold voltage ($V_T$) for the CMOS devices to a higher threshold voltage ($V_T$) value. In this manner, static leakage current losses can be minimized because the equivalent higher threshold voltage has been restored. Further, a broader range of supply voltages is possible because the back gate adjustment allows a tailoring of the threshold allowing high/low speed operation and eliminating the static current drain leakage.

The back gate bias voltage may be provided by, for example, a fixed voltage source (i.e., a charge pump) connected to the back gate well via a contact. Alternatively, an active body bias scheme whereby the voltage source is selectable or adjustable over an appropriate range may be used.

Back gate voltages may be applied in any known manner. For example, the application of back gate bias voltages is described in various patent references including U.S. Pat. No. 4,791,318 to Lewis et al., U.S. Patent No. 4,460,835 to Masuoka, U.S. Pat. No. 5,610,083 to Chan et al., and U.S. Pat. No. 5,185,535 to Farb et al., all incorporated by reference herein in their respective entireties.

Figure 6:
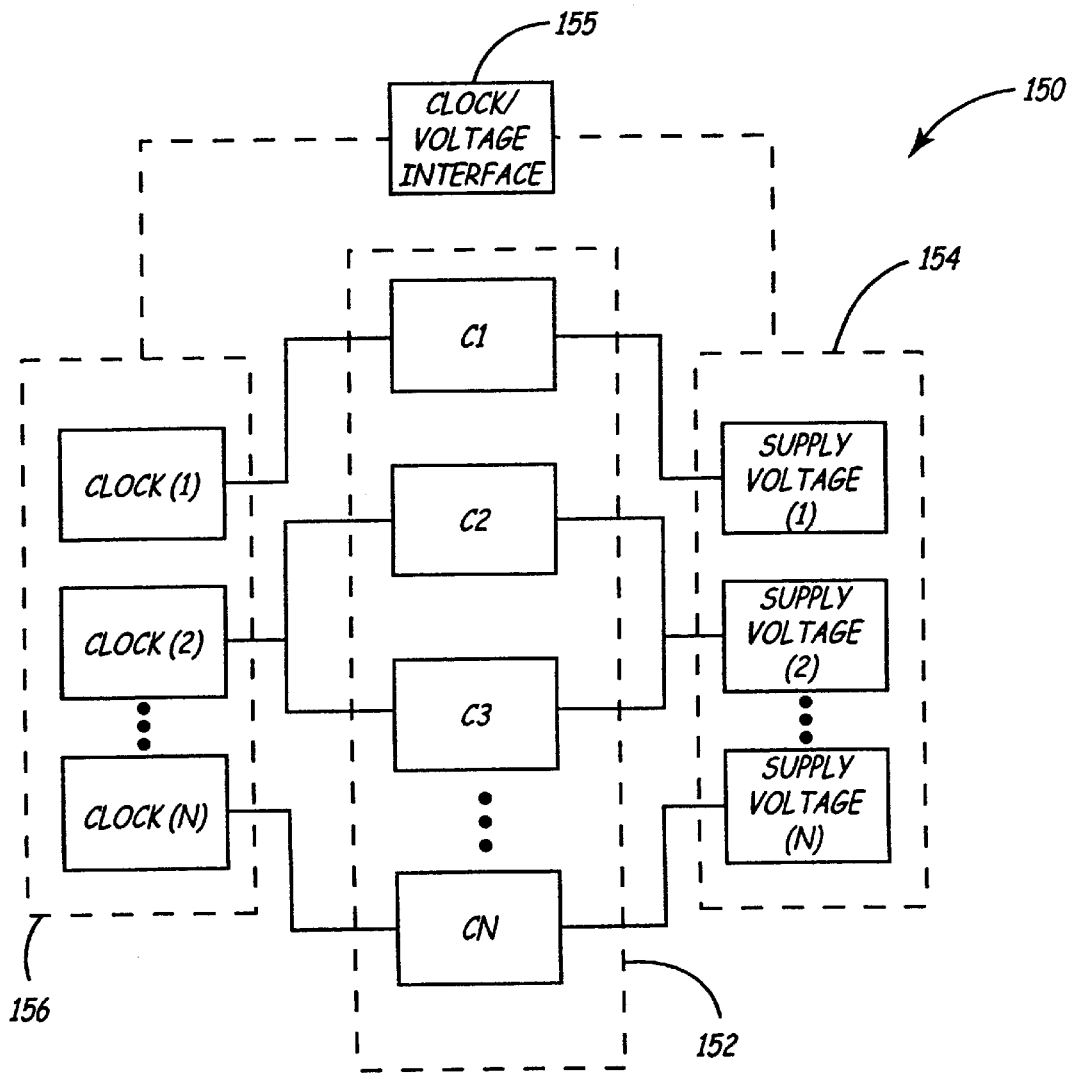
FIG. 6 is a block diagram illustrating a variable supply voltage system according to the present invention.

FIG. 6 shows a general block diagram of a variable supply voltage/variable clock system 150 according to the present invention. The system 150 includes integrated circuit 152, clock source 156, supply voltage source 154, and clock/supply voltage interface 155. Supply voltage source 154 is operable for providing a plurality of supply voltages V1–Vn to a plurality of circuits C1–Cn of integrated circuit 152. Further, the clock source 156 of system 150 is operable for providing clock signals at a plurality of frequencies, clock1–clockn. The circuits C1–Cn are of a similar nature to those described with reference to FIG. 3, the clock source 156 is similar to the clock source 34 as described with reference to FIG. 3, and the supply voltage source 154 is similar to the supply voltage source 106 as described with reference to FIG. 5. However, in the variable supply voltage/variable clock system 150, a clock/voltage interface 155 is used to adjust the supply voltages V1–Vn applied to the circuits C1–Cn "on the fly" as required by specific timing functions required by the circuits C1–Cn.

As an illustrative example, circuit C1 may be a particular logic circuit for performing one or more particular functions.

However, such functions may be required to be performed in a first time period at a first clock frequency and during a different second time period at a second clock frequency to perform such function within the allowed time of the respective first and second time periods. In other words, one time period is shorter than the other and, as such, the functions which require performance over a certain number of cycles must be performed at a higher clock frequency if it is to be completed within a time period that is shorter than another time period. In such an example, according to the present invention, clock/voltage interface 155 detects the clock signal applied to circuit C1 during the first time period in which the higher frequency clock signal is used and accordingly provides supply voltage source 154 with a signal to select and apply a certain supply voltage corresponding to the higher clock frequency. Thereafter, when the lower clock frequency is applied to circuit C1 during the second time period, clock/voltage interface 155 senses the use of the lower clock frequency and applies a signal to voltage supply source 154 for application of a certain supply voltage corresponding to the lower clock frequency for application to circuit C1.

Figure 7:
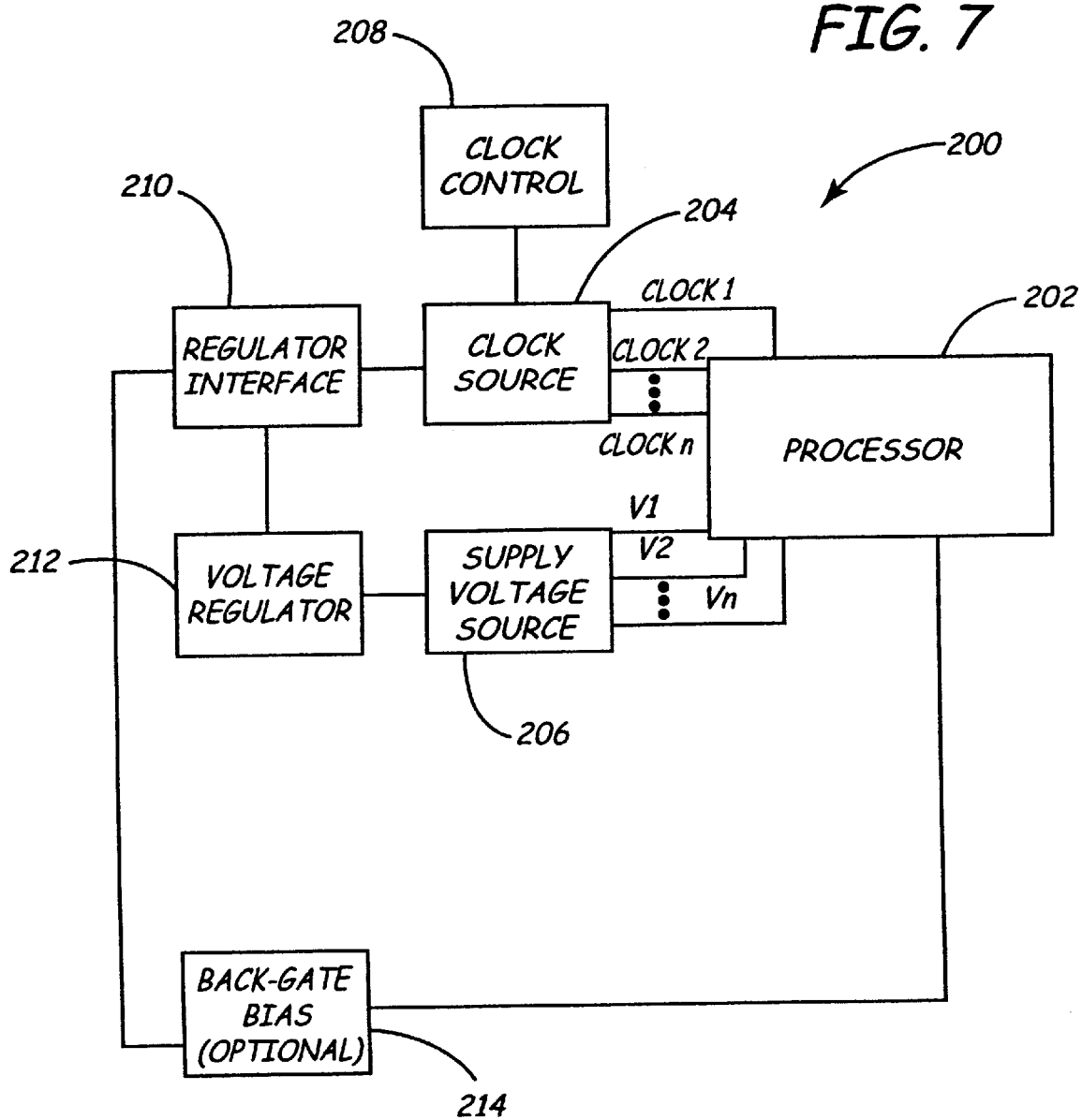
FIG. 7 is a block diagram of clock controlled processing circuitry according to the present invention.

Further, for example, circuit C2 may be a CMOS processor, which may also have clock frequency and corresponding supply voltage adjustments made "on the fly." Such a system will be readily apparent from the discussion to follow with reference to FIG. 7.

FIG. 7 shows a general block diagram of a clock controlled processing system 200 according to the present invention. The clock controlled processing system 200 includes processor 202 (e.g., a CMOS microprocessor or CMOS digital signal processor), clock source 204, supply voltage source 206, voltage regulator 212, regulator interface 210, clock control 208, and optional back gate bias source 214. In a manner similar to that described with reference to FIG. 6, the supply voltage 206 applied to processor 202 is changed "on the fly" as required by specific circuit timing requirements.

Generally, the processor 202 is operated under control of clock source 204. Depending upon the processing capability required, clock source 204 might operate processor 202 at any one of a plurality of clock frequencies. Such clock frequencies will be selected under the control of clock control 208. Clock control 208 may be part of any timing and control hardware and/or timing and control software used to control operation of processor 202 as part of a larger system. For example, such clock control may take the form of a digital controller/timer circuit for performing timing control of an implantable medical device.

Processor 202 may perform any number of functions as appropriate for the device in which it is used. High frequency processing capabilities (i.e., about 250 kHz to about 10 MHz), low frequency processing capabilities (i.e., about 1 Hz to about 32 kHz), and processing capabilities with regard to frequencies between such limits are contemplated according to the present invention. For simplicity purposes, clock control processing system 200 operation shall be described with reference to processor 202 performing only two different functions, each during a predetermined respective period of time. For example, with respect to an implantable medical device such as a pacemaker, during the first period of time, a high processing function requiring a relatively high clock frequency may include a function such as telemetry uplink/downlink, morphology detection, initialization, arrhythmia detection, far-field R-wave detection, EMI detection, retrograde conduction, etc. On the other hand, low frequency processing functions may include a function such as sensing intrinsic beats, pacing, low speed telemetry, transtelephonic data transfer, remote monitoring, battery checks, etc.

When processor 202 during a predetermined time is to perform high frequency processing functions, a relatively high clock frequency, e.g., 250 kHz to 10 MHz, may be supplied by clock source 204 for operation of processor 202. Regulator interface 210 will detect the higher clock frequency applied to processor 202 for operation during the high processing function and apply a control signal to voltage regulator 212 for regulation of the supply voltage source 206. Supply voltage source 206 is operable under control of voltage regulator 212 to provide a supply voltage within a predetermined range, preferably between about 1.1 volts and about 3 volts. When a high clock frequency is used for operation of processor 202 for high frequency processing functions, supply voltage source 206 generally applies a supply voltage in the upper range of the preferred supply voltages to the CMOS devices of processor 202.

On the other hand, when processor 202 is to execute low frequency processing functions during the predetermined periods of time, clock control 208 signals clock source 204 to apply a lower frequency for operation of processor 202. As such, regulator interface 210 detects the lower frequency being used to operate processor 202 and issues a control signal to voltage regulator 212 for regulation of supply voltage source 206 such that a lower supply voltage in the lower end of the preferred range of supply voltages is applied to the CMOS devices of processor 202.

It will be recognized by one skilled in the art that any intermediate processing capability may be achieved between the higher frequency and the lower frequency capabilities described above and that the present invention is in no manner limited to processing at only two clock frequencies and at two corresponding supply voltages. Rather, multiple levels of processing capability can be achieved according to the present invention with associated clock frequencies and corresponding supply voltages being applied to processor 202.

FIG. 4C illustrates one embodiment of the clock control processing system 200. As shown therein, during the overall cardiac cycle of predetermined time period x, a high frequency is used for controlling operation of processor 202 during time period 71 of the cardiac cycle time period x, e.g., during processing of the QRS complex. Thereafter, a lower clock frequency is used during time period y for controlling operation of processor 202 to perform any of a number of other different functions, such as cardiac event/EMI differentiation functions. During operation of the processor 202 at the higher clock frequency during time period 71, a higher supply voltage from supply voltage source 206 is applied to the CMOS devices of processor 202. Likewise, during operation of the processor 202 at the relatively lower clock frequency, a lower supply voltage from supply voltage source 206 is applied to the CMOS devices of processor 202 during time period y of the overall cardiac cycle time period x.

Further, as shown in FIG. 7, an optional back gate bias 214 may be used to dynamically adjust the threshold voltage ($V_T$) of CMOS devices of processor 202 as a function of the clock frequency applied to processor 202 by clock source 204. The regulator interface 210 detects the clock frequency used to control operation of processor 202 and controls the voltage level of back gate bias 214 to be applied to the CMOS devices of processor 202. The dynamic adjustment of the threshold voltage may be implemented as an adjustable or selectable voltage source utilizing, for example, a charge pump and a regulator. The back gate voltage and the "normal" gate voltage provide a gate bias or voltage to the transistor. By adjusting the back gate voltage, the "apparent" voltage is increased with a resultant reduction in leakage current.

Figure 8:
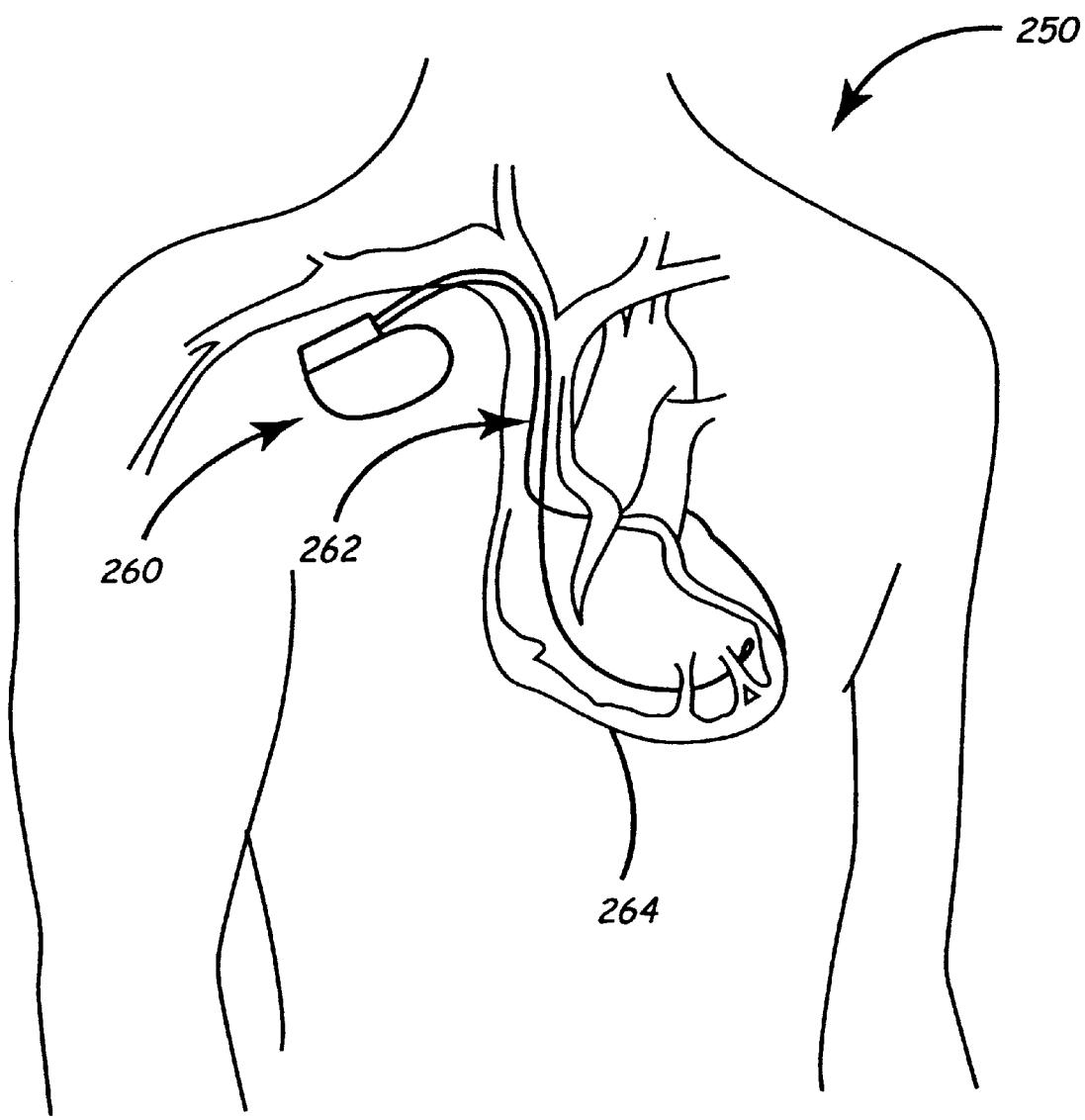
FIG. 8 is a diagram illustrating an implantable medical device in a body.

FIG. 8 is a simplified diagram of an implantable medical device 260 for which the present invention is useful. The implantable device 260 is implanted in a body 250 near a human heart 264. The implanted medical device is connected to the heart by leads 262. In the case where the device 260 is a pacemaker, leads 262 are pacing and sensing leads to sense electrical signals attendant to the depolarization and repolarization of the heart 264 and provide pacing pulses in the vicinity of the distal ends thereof. Implantable medical device 260 may be any implantable cardiac pacemaker such as those disclosed in U.S. Pat. No. 5,158,078 to Bennett et al., U.S. Pat. No. 5,312,453 to Shelton et al., or U.S. Pat. No. 5,144,949 to Olson, all hereby incorporated herein by reference in their respective entireties and which can all be modified according to the present invention.

Figure 10:
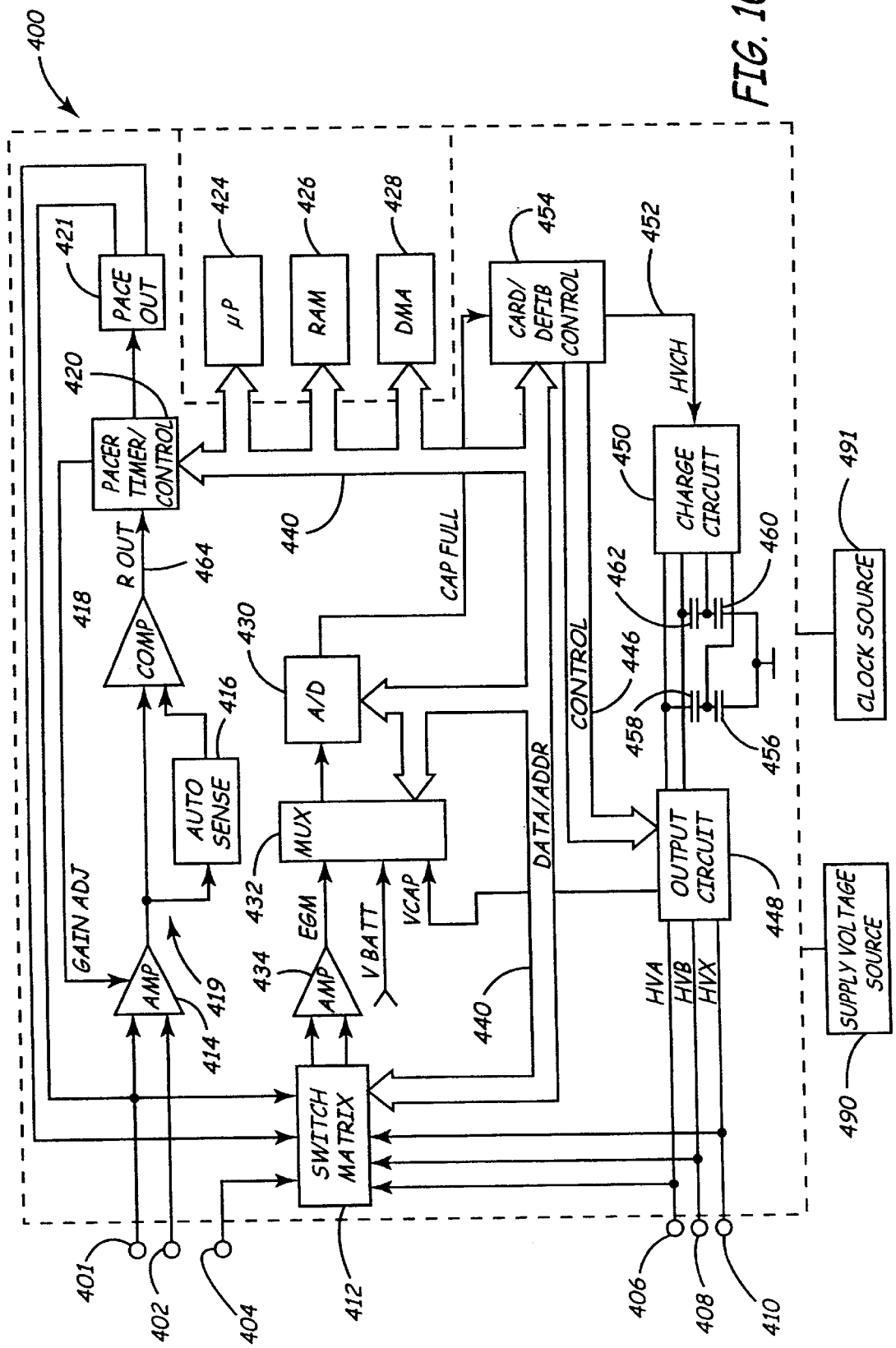
FIG. 10 is a schematic block diagram of an implantable pacemaker/cardioverter/defibrillator (PCD) for use in illustrating one or more embodiments of the present invention.

Implantable medical device 260 may also be a pacemaker/cardioverter/defibrillator (PCD) corresponding to any of the various commercially-available implantable PCDs, one of which is summarily described herein with reference to FIG. 10 and described in detail in U.S. Pat. No. 5,447,519. In addition to the PCD described in U.S. Pat. No. 5,447,519, the present invention may be practiced in conjunction with PCDs such as those disclosed in U.S. Pat. No. 5,545,186 to Olson et al., U.S. Pat. No. 5,354,316 to Keimel, U.S. Pat. No. 5,314,430 to Bardy, U.S. Pat. No. 5,131,388 to Pless, or U.S. Pat. No. 4,821,723 to Baker et al., all hereby incorporated herein by reference in their respective entireties. Those devices may be employed using the present invention in that such devices may employ or be modified with circuitry and/or systems according to the present invention.

Alternatively, implantable medical device 260 may be an implantable nerve stimulator or muscle stimulator such as those disclosed in U.S. Pat. No. 5,199,428 to Obel et. al., U.S. Pat. No. 5,207,218 to Carpentier et al., or U.S. Pat. No. 5,330,507 to Schwartz, or an implantable monitoring device such as that disclosed in U.S. Pat. No. 5,331,966 issued to Bennet et al., all of which are hereby incorporated by reference herein in their respective entireties. The present invention is believed to find wide application to any form of electrical device which uses CMOS circuit design and is believed to be particularly advantageous where low power is desired, particularly in implantable medical devices.

In general, the implantable medical device 260 includes a hermetically-sealed enclosure that includes an electrochemical cell such as a lithium battery, CMOS circuitry that controls device operations, and a telemetry transceiver antenna and circuit that receives downlinked telemetry commands from and transmits stored data in a telemetry uplink to an external programmer. The circuitry may be implemented in discrete logic and/or may include a microcomputer-based system with A/D conversion.

It is to be understood that the present invention is not limited in scope to particular electronic features and operations of particular implantable medical devices and that the present invention may be useful in conjunction with various implantable devices. Further, the present invention is not limited in scope to implantable medical devices including only a single processor but may be applicable to multiple-processor devices as well.

Figure 9:
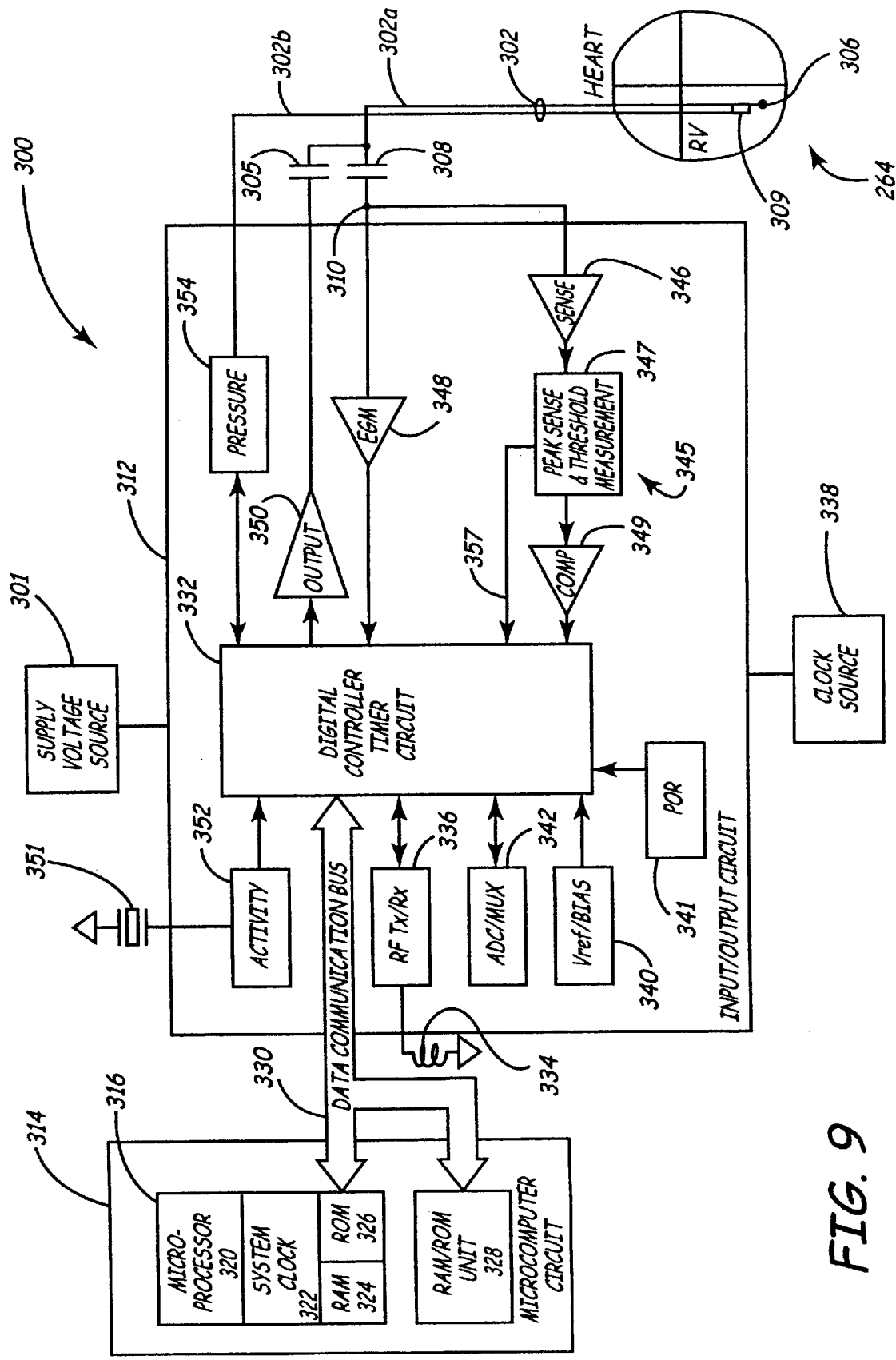
FIG. 9 is a block diagram of the circuitry of a pacemaker for use in illustrating one or more embodiments of the present invention.

FIG. 9 shows a block diagram illustrating the components of a pacemaker device 300 in accordance with one embodiment of the present invention. Pacemaker device 300 has a microprocessor-based architecture. However, the illustrative pacemaker device 300 of FIG. 9 is only one exemplary embodiment of such devices and it will be understood that it could be implemented in any logic-based, custom integrated circuit architecture, if desired, as can any microprocessor-based system.

In the illustrative embodiment shown in FIG. 9, the pacemaker device 300 is most preferably programmable by means of an external programming unit (not shown in the figures). One such programmer suitable for the purposes of the present invention is the commercially available Medtronic Model 9790 programmer. The programmer is a microprocessor-based device which provides a series of encoded signals to pacemaker device 300 by means of a programming head which transmits radio frequency (RF) encoded signals to antenna 334 of pacemaker device 300 according to a telemetry system such as, for example, that described in U.S. Pat. No. 5,127,404 to Wyborny et al., the disclosure of which is hereby incorporated by reference herein in its entirety. It is to be understood, however, that any programming methodology may be employed so long as the desired information is transmitted to and from the pacemaker.

Pacemaker device 300 illustratively shown in FIG. 9 is electrically coupled to the patient's heart 264 by leads 302. Lead 302a including electrode 306 is coupled to a node 310 in the circuitry of pacemaker device 300 through input capacitor 308. Lead 302b is coupled to pressure circuitry 354 of input/output circuit 312 to provide a pressure signal from sensor 309 to the circuit 354. The pressure signal is used to ascertain metabolic requirements and/or cardiac output of a patient. Further, activity sensor 351, such as a piezoceramic accelerometer, provides a sensor output to activity circuit 352 of input/output circuit 312. The sensor output varies as a function of a measured parameter that relates to metabolic requirements of a patient. Input/output circuit 312 contains circuits for interfacing to heart 264, to activity sensor 351, to antenna 334, to pressure sensor 309 and circuits for application of stimulating pulses to heart 264 to control its rate as a function thereof under control of software-implemented algorithms in microcomputer unit 314.

Microcomputer unit 314 preferably comprises on-board circuit 316 that includes microprocessor 320, system clock circuit 322, and on-board random access memory (RAM) 324 and read only memory (ROM) 326. In this illustrative embodiment, off-board circuit 328 comprises a RAM/ROM unit. On-board circuit 316 and off-board circuit 328 are each coupled by a communication bus 330 to digital controller/timer circuit 332.

According to the present invention, the circuits shown in FIG. 9 are powered by an appropriate supply voltage source 301 (e.g., a voltage source generally shown in FIGS. 1–7). For the sake of clarity, the coupling of supply voltage source 301 to various circuits of pacemaker device 300 is not shown in the figures. Further, the circuits operable under control of a clock signal shown in FIG. 9 are operated according to the present invention under clock source 338. For the sake of clarity, the coupling of such clock signals from the clock source 338 (e.g., a clock source generally shown in FIGS. 1–7) to such CMOS circuits of the pacemaker device 300 is not shown in the figures.

Antenna 334 is connected to input/output circuit 312 to permit uplink/downlink telemetry through RF transmitter and receiver unit 336. Unit 336 may correspond to the telemetry and program logic disclosed in U.S. Pat. No. 4,556,063 issued to Thompson et al., hereby incorporated by reference herein in its entirety, or to that disclosed in the above-referenced Wyborny et al. patent.

$V_{REF}$ and bias circuit 340 generates a stable voltage reference and bias currents for circuits of input/output circuit 312. Analog-to-digital converter (ADC) and multiplexer unit 342 digitize analog signals and voltages to provide "real-time" telemetry intracardiac signals and battery end-of-life (EOL) replacement function. A power on reset circuit 341 functions as a means to reset circuitry.

Operating commands for controlling the timing of pacemaker device 300 are coupled by bus 330 to digital controller/timer circuit 332, where digital timers and counters establish the overall escape interval of the pacemaker device 300 as well as various refractory, blanking, and other timing windows for controlling the operation of the peripheral components disposed within input/output circuit 312.

Digital controller/timer circuit 332 is preferably coupled to sense circuitry 345 and to electrogram (EGM) amplifier 348 for receiving amplified and processed signals sensed by electrode 306 disposed on lead 302a. Such signals are representative of the electrical activity of the patient's heart 264. Sense amplifier 346 of circuitry 345 amplifies sensed electrocardiac signals and provides an amplified signal to peak sense and threshold measurement circuitry 347. Circuit 347 in turn provides an indication of peak sensed voltages and measured sense amplifier threshold voltages on path 357 to digital controller/timer circuit 332. An amplified sense amplifier signal is also provided to comparator/threshold detector 349. Sense amplifier 346 may correspond to that disclosed in U.S. Pat. No. 4,379,459 to Stein, which is hereby incorporated by reference herein in its entirety.

The electrogram signal provided by EGM amplifier 348 is employed when the implanted device 300 is being interrogated by an external programmer (not shown) to transmit by uplink telemetry a representation of an analog electrogram of the patient's electrical heart activity. Such functionality is, for example, shown in U.S. Pat. No. 4,556,063 to Thompson et al., previously incorporated by reference.

Output pulse generator and amplifier 350 provides pacing stimuli to the patient's heart 264 through coupling capacitor 305 and electrode 306 in response to a pacing trigger signal provided by digital controller/timer circuit 332. Output amplifier 350 may correspond generally to the output amplifier disclosed in U.S. Pat. No. 4,476,868 to Thompson, also incorporated by reference herein in its entirety. The circuits of FIG. 9 which are CMOS circuitry capable of operation according to the present invention include processor 320, digital controller timer circuit 332, RAM 324, ROM 326, RAM/ROM unit 328 and ADC/Mux 342.

FIG. 10 is a functional schematic diagram from U.S. Pat. No. 5,447,519 to Peterson, which shows an implantable PCD 400 in which the present invention may usefully be practiced. This diagram is an illustration to be taken only as an exemplary type of device in which the invention may be embodied, and not as limiting to the scope of the present invention. Other implantable medical devices as previously described having functional organizations wherein the present invention may be useful may also be modified in accordance with the present invention. For example, the present invention is also believed to be useful in conjunction with implantable PCDs as disclosed in prior U.S. Pat. No. 4,548,209 to Wielders et al.; U.S. Pat. No. 4,693,253 to Adams et al.; U.S. Pat. No. 4,830,006 to Haluska et al.; and U.S. Pat. No. 4,949,730 to Pless et al.; all of which are incorporated herein by reference in their entireties.

The illustrative PCD device 400 is provided with six electrodes 401, 402, 404, 406, 408, and 410. For example, electrodes 401 arid 402 may be a pair of closely-spaced electrodes positioned in the ventricle of the heart 264. Electrode 404 may correspond to a remote, indifferent electrode located on the housing of the implantable PCD 400. Electrodes 406, 408, and 410 may correspond to large surface area defibrillation electrodes located on leads to the heart 264 or epicardial electrodes.

Electrodes 401 and 402 are shown as hard-wired to the near field (i.e., narrowly spaced electrodes) R-wave detector circuit 419 comprising band pass filtered amplifier 414, auto threshold circuit 416 (for providing an adjustable sensing threshold as a function of the measured R-wave amplitude), and comparator 418. A Rout signal 464 is generated whenever the signal sensed between electrodes 401 and 402 exceeds a sensing threshold defined by auto threshold circuit 416. Further, the gain on amplifier 414 is adjusted by pacer timer and control circuitry 420. The sense signal, for example, is used to set the timing windows and to align successive waveshape data for morphology detection purposes. For example, the sense event signal 464 may be routed through the pacer/timer control circuit 420 on bus 440 to processor 424 and may act as an interrupt for the processor 424 such that a particular routine of operations, e.g., morphology detection, discrimination functions, is commenced by processor 424.

Switch matrix 412 is used to select available electrodes under control of processor 424 via data/address bus 440 such that the selection includes two electrodes employed as a far field electrode pair (i.e., widely spaced electrodes) in conjunction with a tachycardia/fibrillation discrimination function (e.g., a function to discriminate between tachycardia, i.e., an abnormally fast heart rate, and fibrillation, i.e., uncoordinated and irregular heartbeats, so as to apply an appropriate therapy). Far field EGM signals from the selected electrodes are passed through band pass amplifier 434 and into multiplexer 432, where they are converted to digital data signals by analog to digital converter (ADC) 430 for storage in random access memory 426 under control of direct memory access circuitry 428. For example, a series of EGM complexes for several seconds may be performed.

According to the present invention, the circuits shown in FIG. 10 are powered by an appropriate supply voltage source 490 (e.g., a voltage source generally shown in FIGS. 1–7). For the sake of clarity, the coupling of supply voltage source 490 to various circuits of the PCD device 400 is not shown in the figures. Further, the circuits operable under control of a clock signal shown in FIG. 10 are operated according to the present invention under clock source 491. For the sake of clarity, the coupling of such clock signals from the clock source 491 (e.g., a clock source generally shown in FIGS. 1–7) to such CMOS circuits of the PCD device 400 is not shown in the figures.

The occurrence of an R-wave sense event or detect signal Rout 464 is communicated to processor 424 to initiate morphology analysis on waveforms by processor 424 for use in selection of a therapy for heart 264. For example, the processor may calculate the cumulative beat-to-beat variability of heart 264, time intervals separating R-wave sense events, and various other functions as set out in numerous references including any of the references already listed herein and various other references with regard to implantable PCDs.

Other portions of the PCD device 400 of FIG. 10 are dedicated to the provision of cardiac pacing, cardioversion, and defibrillation therapies. With regard to cardiac pacing, the pacer timing/control circuit 420 includes programmable digital counters which control the basic timing intervals associated with cardiac pacing, including the pacing escape intervals, the refractory periods during which sensed R-waves are ineffective to restart timing of escape intervals, etc. The durations of such intervals are typically determined by processor 424 and communicated to pacer timer/control circuit 420 via address/data bus 440. Further, under control of processor 424, pacer timing/control circuit also determines the amplitude of such cardiac pacing pulses and pace out circuit 421 provides such pulses to the heart.

In the event that a tachyarrhythmia (i.e., tachycardia) is detected, and an anti-tachyarrhythmia pacing therapy is desired, appropriate timing intervals for controlling generation of anti-tachycardia pacing therapies are loaded from processor 424 into pacer timing and control circuitry 420. Similarly, in the event that generation of a cardioversion or defibrillation pulse is required, processor 424 employs the counters and timing and control circuitry 420 to control timing of such cardioversion and defibrillation pulses.

In response to detection of fibrillation or a tachycardia requiring a cardioversion pulse, processor 424 activates cardioversion/defibrillation control circuitry 454, which initiates charging of the high voltage capacitors 456, 458, 460 and 462 via charging circuit 450 under control of high voltage charging line 452. Thereafter, delivery of the timing of the defibrillation or cardioversion pulse is controlled by pacer timing/control circuitry 420. Various embodiments of an appropriate system for delivering and synchronization of cardioversion and defibrillation pulses, and controlling the timing functions related to them is disclosed in more detail in U.S. Pat. No. 5,188,105 to Keimel, which is incorporated herein by reference in its entirety. Other such circuitry for controlling the timing and generation of cardioversion and defibrillation pulses is disclosed in U.S. Pat. No. 4,384,585 to Zipes, U.S. Pat. No. 4,949,719 to Pless et al., and in U.S. Pat. No. 4,375,817 to Engle et al., all incorporated herein by reference in their entireties. Further, known circuitry for controlling the timing and generation of anti-tachycardia pacing pulses is described in U.S. Pat. No. 4,577,633 to Berkovits et al., U.S. Pat. No. 4,880,005 to Pless et al., U.S. Pat. No. 4,726,380 to Vollmann et al., and U.S. Pat. No. 4,587,970 to Holley et al., all of which are incorporated herein by reference in their entireties.

Selection of. a particular electrode configuration for delivery of the cardioversion or defibrillation pulses is controlled via output circuit 448 under control of cardioversion/defibrillation control circuit 454 via control bus 446. Output circuit 448 determines which of the high voltage electrodes 406, 408 and 410 will be employed in delivering the defibrillation or cardioversion pulse regimen.

The components of the PCD device 400 of FIG. 10 which are CMOS circuitry capable of operation according to the present invention include processor 424, control circuits 420 and 454, RAM 426, DMA 428, ADC 430, and multiplexer 432.

According to the present invention, the pacemaker device 300 illustrated in FIG. 9 and the PCD device 400 illustrated in FIG. 10 may both be implemented in accordance with the generalized embodiments previously described herein with reference to FIGS. 1–7. First, for example, with respect to the pacemaker device 300 of FIG. 9, the voltage supply source 301 of the pacemaker device 300 may be implemented in a manner previously described with reference to FIGS. 1–7 and, likewise, clock source 338 of pacemaker device 300 may be implemented in such a manner as described with reference to FIGS. 1–7. Likewise, clock source 491 of the PCD device 400 of FIG. 10 and the voltage supply source 490 of the PCD device 400 of FIG. 10 may be implemented in accordance with the generalized embodiments previously described herein with reference to FIGS. 1–7.

As one illustrative example, the ADC/mux 342, the RF transmitter/receiver 336, digital controller timer circuit 332, and various other CMOS circuits may be individually operated at different clock frequencies available from clock source 338. Likewise, such circuits may be operated at corresponding supply voltages, which may be different for each of the circuits. Further, for example, RF transmitter/receiver 336 may be operated during a particular time period (e.g., when uplinking) at a particular clock frequency available from clock source 338 and at a particular supply voltage available from voltage supply source 301 corresponding to the particular clock frequency. On the other hand, during a different time period (e.g., during downlink), the circuit 336 may be operated at a completely different clock frequency and supply voltage. Automatic adjustment of telemetry parameters under certain circumstances is described in U.S. Pat. No. 5,683,432 to Goedeke et al.

Further, with respect to FIG. 10, A/D converter circuit 430, cardioverter/defibrillator control circuit 454, and various other circuits such as RAM 426, DMA 428, and multiplexer 432 may also be operated at different clock frequencies available from clock source 491 and at different corresponding supply voltages available from supply voltage source 490. Further, a telemetry circuit (not shown) may be used with the PDA of FIG. 10 and may also be operated at different clock frequencies available from clock source 491 and at different corresponding supply voltages available from supply voltage source 490. In addition, processor 424 may be operated at different clock speeds depending upon the function being performed by the processor 424, such as described with reference to FIG. 7 herein. For example, morphology detection sensing at typical physiologic rates (i.e., 50 to 150 BPM) may be performed at a first clock frequency and corresponding supply voltage while arrhythmia detection may be performed at a different clock frequency and corresponding supply voltage.

Figure 11:
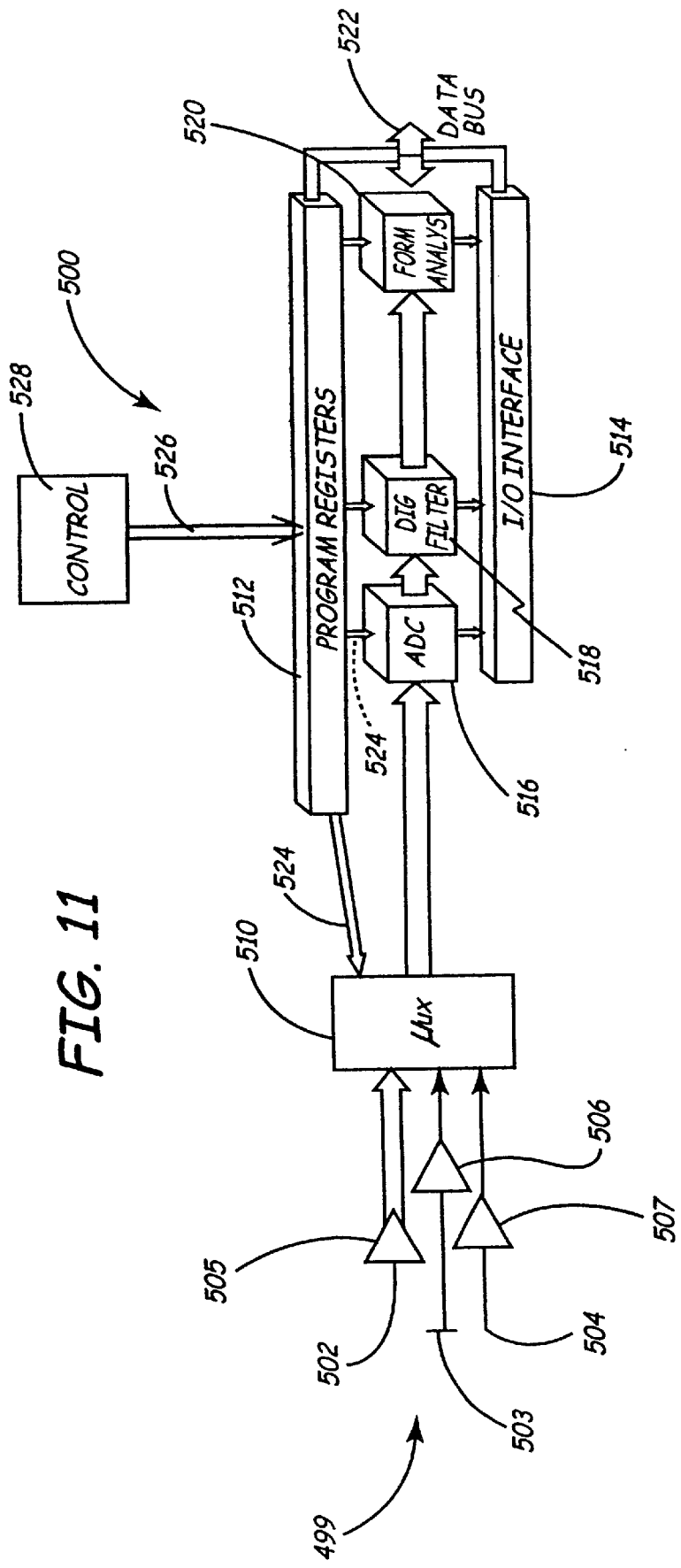
FIG. 11 is a schematic block diagram illustrating a variable clock/variable supply voltage digital signal processing system according to the present invention.

FIG. 11 shows a variable clock/variable supply voltage digital signal processing system 500 which may be used in conjunction with and/or in the alternative to certain circuits shown in FIGS. 9 and 10. For example, the digital signal processing system 500 according to FIG. 11 may be used in place of activity circuit 352, pressure circuit 354, sense amplifier circuit 346 (for P-wave, R-wave- and/or T-wave sense amplifiers), and further may be provided with additional functionality with use of a pseudo EKG signal 502. Generally, any number of analog signals 499, for example, such as pseudo EKG signals 502, activity sensor signal 503 and pressure and onset sensor signal 504, are provided through respective amplifiers 505–507. The amplified signals are presented to multiplexer 510 which provides them to analog to digital converter (ADC) 516 in a cycled fashion. The signals 502–504 can be cycled at different rates by cycling through the outputs of the several amplifiers/preamplifiers 505–507 such as described in pending U.S. patent application Ser. No. 08/801,335, Medtronic Docket No. P-4521, entitled "Method for Compressing Digitized Cardiac Signals Combining Lossless Compression and Nonlinear Sampling," which describes variable compression via ADC sampling and which is incorporated herein by reference in its entirety. The ADC may also have variable conversion rates as described in U.S. Pat. No. 5,263,486 and U.S. Pat. No. 5,312,446 which are also incorporated herein by reference in their entireties.

Input/output interface 514 and program registers 512 are utilized under control of a timing circuit (not shown) to control application of the analog signals from multiplexer 510 to ADC 516 which provides such converted digital signals to digital filter 518 to provide a waveform for analysis to waveform analysis processor 520 (i.e., a digital signal processor (DSP)). To reduce power, the waveform analysis processor 520 is clocked at different speeds, i.e., controlled "on the fly," according to the present invention, depending upon the processing needs. For example, only during a QRS complex will the waveform analysis processor 520 be in a high speed processing mode at a relatively high frequency, while during the remainder of the cardiac cycle the processor 520 may be "idling along" at a much lower clock frequency. Such a processing cycle has been previously described with reference to FIG. 4C. In addition to the lower clock speed utilized for different portions of the cardiac cycle, one skilled in the art will recognize that in accordance with the other aspects of the present invention, as the speed is reduced, the supply voltage level ($V_{DD}$) may also be reduced accordingly. Thus, reduced power consumption is attained as previously described.

Figure 12:
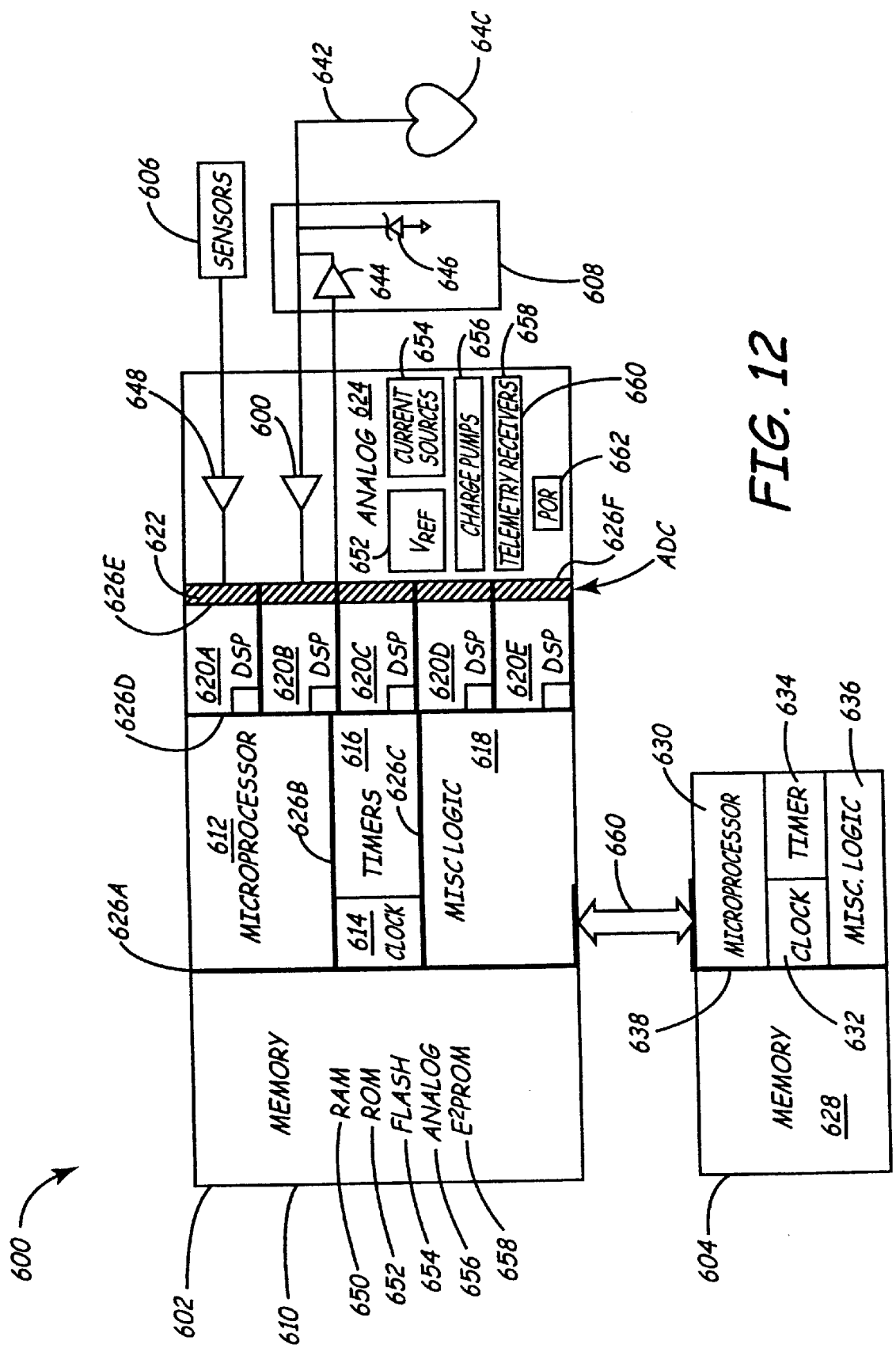
FIG. 12 is a schematic block diagram illustrating an implantable medical device according to the present invention.

FIG. 12 is a schematic block diagram illustrating implantable medical device 600 according to the present invention. Implantable medical device 600 further includes integrated circuit 602, integrated circuit 604, sensors 606, and output integrated circuit 608. Integrated circuit 602 further includes memory 610, microprocessor 612, clock 614, timer 616, miscellaneous logic 618, digital signal processors 620A–620E, analog-to-digital converters 622, and analog circuitry 624. Integrated circuit 604 further comprises memory 628, microprocessor 630, clock 632, timer 634, and miscellaneous logic 636.

Implantable medical device 600 is implanted into a patient in. proximity to heart 640 by employing techniques such as those previously described with references to FIGS. 8 and 9. Implantable medical device 600 can be embodied as any one of a variety of implantable medical devices, such as those previously discussed, including a pacemaker or a defibrillator. Implantable medical device 600 is connected to heart 640 via leads 642. Leads 642 can be pacing or sensing leads that provide electrical stimulation to the heart in accordance with the present invention.

Output integrated circuit 608 provides two specific functions. First, heart 640 is stimulated by output integrated circuit 608, which provides a voltage pulse signal in a range of 0.5–10 volts. Second, output integrated circuit 608 protects various elements of implantable medical device 600, such as integrated circuit 602 and 604 and their sub-components, from defibrillation and electrocautery pulses picked up from lead 642. Without such protection, defibrillation and electrocautery pulses from lead 642 would damage integrated circuits 602 and 604, which operate at low voltage levels. The various sub-components of integrated circuits 602 and 604 are not designed to operate with such large voltage levels present in the defibrillation and electrocautery pulses (i.e., greater than 15 volts). In one preferred embodiment, output integrated circuit 608 includes amplifier 644 and zener diode 646. Amplifier 644 amplifies the signal from integrated circuit 602 provided to heart 640 via leads 642. Zener diode 646 prevents large voltages (i.e., greater than 10 volts) from returning to integrated circuit 602 after lead 642 has been energized. In one embodiment, output integrated circuit 608 is implemented in CMOS technology, which has a very high breakdown voltage and drive capability (i.e. greater than 3 micron technology).

Sensors 606 can be any of a variety of sensors, such as an accelerator sensor, pressure sensor, temperature sensor, oxygen saturation sensor, etc. sensors, or any combination thereof, depending upon the type of implantable medical device and the needs of the patient. Analog circuitry 624 includes amplifiers 648 and 650 which amplify signals from sensors 606 and, when necessary, signals from leads 642, respectively. Analog circuitry 624 also includes various sub-components, such as reference voltage 652, current sources 654, charge pumps 656, telemetry drivers 658, telemetry receivers 660, and power on reset (POR) 662.

Analog circuitry 624 is connected to analog-to-digital converter 622 via bus 626F. In one preferred embodiment, bus 626F is a standard 8-bit bus. However, it is understood that bus 626F can be any of a variety of buses without varying from the present invention. Analog-to-digital converter 622 receives an analog input signal and provides a digital output signal representative of the signal amplitude. In one preferred embodiment, analog-to-digital converter 622 can be replaced by a plurality of analog-to-digital converters.

Analog-to-digital converter 622 is connected to digital signal processors 620A–620E, via bus 626E. In one preferred embodiment, bus 626E is a standard 8-bit bus. However, it is understood that bus 626E can be any of a variety of buses without varying from the present invention. Digital signal processors 620A–620E perform a variety of parallel functions, such as sensing atrial and ventricular signals, detect arrythmias, process sensor signals, etc.

Memory 610, microprocessor 612, clock 614, timer 616, miscellaneous logic 618, and digital signal processors 620A–620E are all interconnected via buses 626A–626D. These components provide various functions necessary for implantable medical device 600 to operate properly. More specifically, memory 610 may be used to store various bits of information such as a program code, parametric variables, and diagnostic data in memory components such as RAM 650, ROM 652, flash memory 654, analog memory 656, and $E^2PROM$ 658. Microprocessor 612 is a standard component which processes information received from memory 610 or heart 640. Clock 614 generates a clock signal and provides the clock signal to various sub-components of implantable medical device 600, such as microprocessor 612 and timers 616.

Timers 616 are resident devices, which provide proper timing sequences to various sub-components of implantable medical device 600, such as microprocessor 612. Miscellaneous logic 618 includes various logic components including clock powered dynamic supplies and clocks. Miscellaneous logic 618 provides interface and control between microprocessors, timers, analog clocks, and DPSs. Memory 628, microprocessor 630, clock 632, timer 634, and miscellaneous logic 636 of integrated circuit 604 provide similar functions to their counterpart components of integrated circuit 602. In one preferred embodiment, integrated circuit 604 includes expanded memory functions for storing information related to the programming of implantable medical device 600 and information received from sensors 606 for a 24-hour period. Integrated circuit 602 is connected to integrated circuit 604 via bus 660. Similar to previously discussed buses, in one preferred embodiment, bus 660 is a standard 8-bit bus, but can be any of a variety of buses known in the art.

Minimization and control of power dissipation is one of the significant aspects of the present invention. Specifically, efficient implementation of power systems in implantable medical device 600 enables conservation of space and volume in addition to reduction in weight while maintaining a desired output. Low efficiency results in higher costs, primarily because of a waste of energy and the need for larger power supplies. For example, dynamic power (P) of a given circuit of implantable medical device 600 is equal to: ½ $CV_{DD}^2 F$, where C is the nodal capacitance of the circuit, F is the clock frequency of the circuit, and $V_{DD}$ is the supply voltage for the circuit. Medical device 600, according to the present invention, utilizes a relatively low system clock frequency to generate various logic signals. Use of a relatively low system clock frequency, preferably less than 500 kHz, enables substantial reduction in power dissipation.

Battery life is a major factor in implantable medical device 600. However, battery life extension often requires the use of large and heavy batteries. Large batteries are not conducive to use in implantable medical devices because they adversely impact the size and weight of the implanted device.

In addition, dissipated energy is released in the form of heat. Accordingly, prior art devices with considerable power dissipation often require cooling mechanisms, such as heat sinks, to protect heat sensitive system components from damage or malfunction. Generally, heat sinks add to the cost, size, and weight of a device and are one of the most significant limitations of the prior art.

The invention incorporates adiabatic logic at various points within implantable medical device 600 to minimize power dissipation, thereby producing a more efficient device. The term "adiabatic" is defined herein as a thermal dynamic process that has no energy exchange with the surrounding environment, and therefore no dissipation energy is released in the form of heat. In the embodiments shown in FIGS. 13 and 15–17, various circuits are shown which create a stepwise voltage ramp across an internal capacitance associated with a standard bus. In one embodiment, the standard bus is positioned between two or more integrated circuit chips (i.e., chip to chip), and in another embodiment, the standard bus is positioned between specific components of a single integrated circuit. The embodiments shown in FIGS. 13 and 15–17 can be used in conjunction with an internal capacitance associated with a variety of buses, such as buses 626A–626F, 638, and 660 illustrated in FIG. 12. As shown in FIG. 12, buses 626A–626F and 638 are buses within a single integrated circuit interconnecting various components of integrated circuit 602 or integrated circuit 604. Conversely, bus 660 interconnects integrated circuit 602 with integrated circuit 604.

Figure 20:
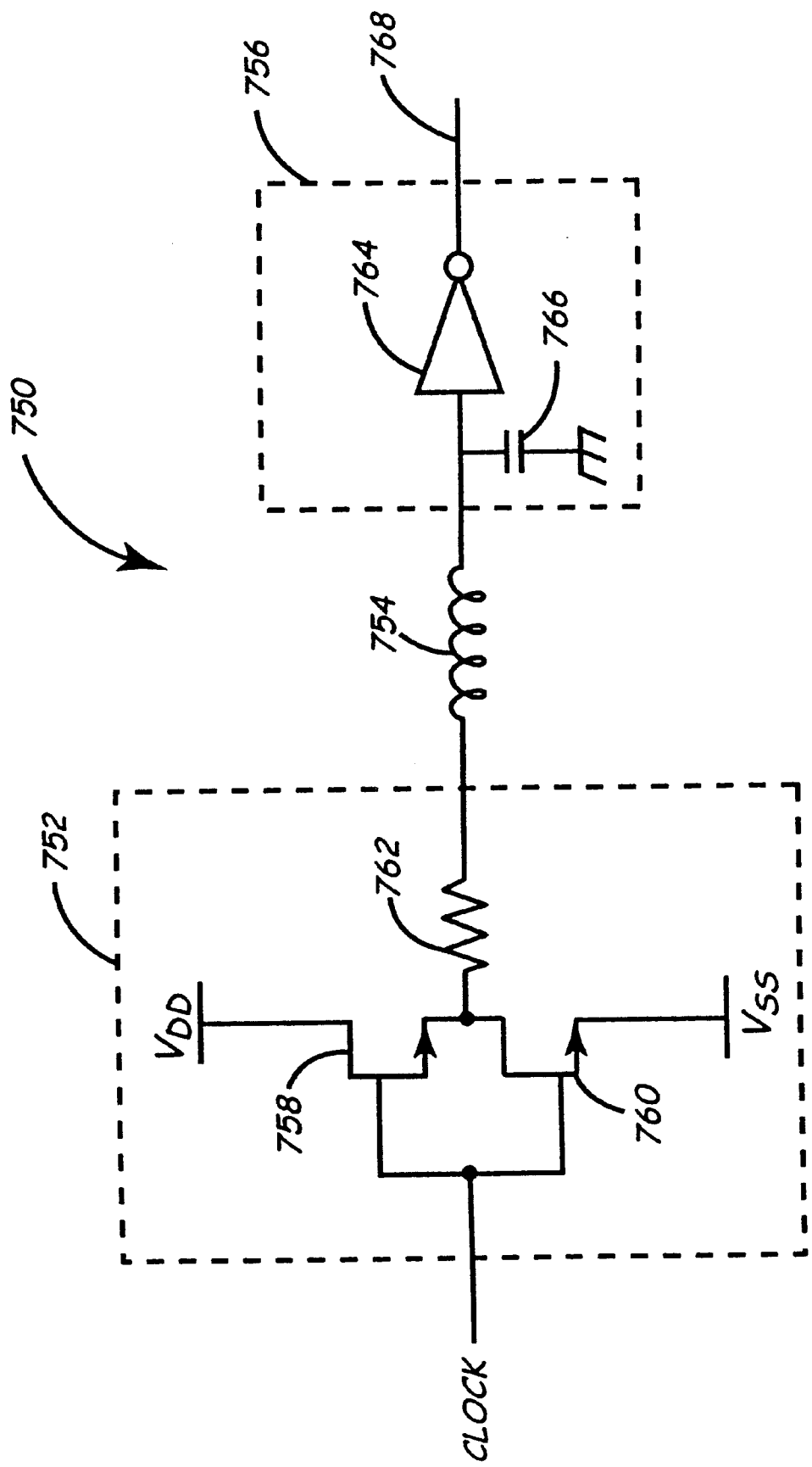
FIG. 20 is a circuit diagram illustration yet another embodiment of the present invention utilizing adiabatic logic within the implantable medical device.

As will be discussed in more detail below, various circuits in medical device 600 minimize energy dissipation by using adiabatic logic during a change in a signal state. For example, FIGS. 13 and 15–17 illustrate various embodiments in which a stepwise voltage ramp is used to prevent excessive leakage current during a switching operation. Alternatively, FIG. 18 illustrates circuitry which provides a constant current ramp to charge and discharge a nodal capacitor. Also, FIG. 20 illustrates circuitry which provides minimal power dissipation through use of a series inductor with an internal capacitance associated with a clock drive buffer.

Figure 13:
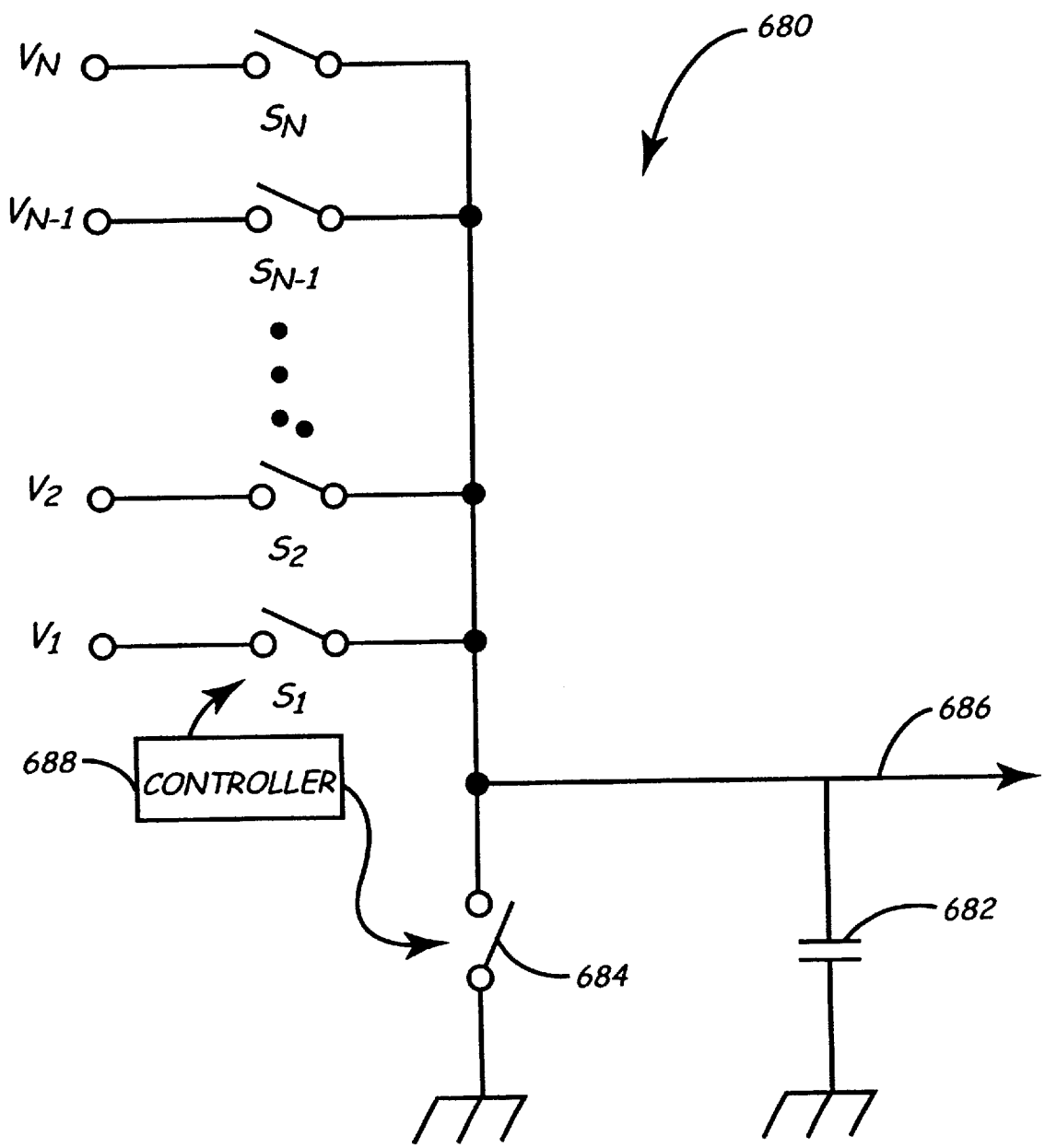
FIG. 13 is a circuit diagram illustrating an embodiment of the present invention utilizing adiabatic logic for use within the implantable medical device.

Adiabatic logic circuitry 680, shown in FIG. 13, is one embodiment of a charging circuit implemented to minimize power dissipation during a switching operation of a clock through use of adiabatic logic. Circuitry 680 operates at a relatively low clock frequency, such as less than 500 kilohertz. Circuitry 680 can be used in conjunction with any of the buses shown in FIG. 12. Depending upon the particular bus connection, circuit 680 is capable of supplying a logic signal in either direction (e.g., with respect to bus 660, a logic signal can be sent from integrated circuit 602 to integrated circuit 604 or vice versa). As shown in FIG. 13, circuit 680 includes capacitor 682, switch 684, controller 688, switches $S_1$–$S_N$, and voltages $V_1$–$V_N$. In one preferred embodiment, capacitor 682 is not a separate physical component, but rather is an internal capacitance comprising the total capacitance of the internal nodes connected to a bus, such as bus 660.

Controller 688 is a standard controller known in the art. Controller 688 controls the operation of switches $S_1$–$S_N$ and switch 684 by logic level changes. Circuitry 680 charges capacitor 682 through several intermediate steps to thereby produce ramped logic signal 686, which is transmitted to various sub-components of implantable medical device 600. Ramped logic signal 686 is adiabatic in nature, which minimizes power dissipation thereby increasing the useful lifetime of the battery and implantable medical device 600. Ramped logic signal 686 provides timing sequences to various sub-components of implantable medical device 600, such as microprocessors 612 and 630. Prior art devices change in a single abrupt state, which produces dissipation energy in the form of increased current drain of the device. By contrast, the timing sequences provided by ramped logic signal 686 according to the invention cause the sub-components receiving ramped logic signal 686 to gradually change states to thereby reduce dissipation energy over prior art designs.

Supply voltages $V_1$–$V_N$ are used to charge capacitor 682. In one preferred embodiment, supply voltages $V_1$–$V_N$ are evenly distributed between ground and $V_N$ so that the voltage difference between any two adjacent supplies is the same. Each of the supply voltages is selectively applied to capacitor 682 by N switches including the first switch $S_1$ and N−1 additional switches. To reset the voltage on capacitor 684 to an initial condition, switch 684 is closed. To charge the load, switch 684 is opened and supply voltages $V_1$–$V_N$ are connected to capacitor 682 in succession by selectively closing the switches, that is, by momentarily closing switch $S_1$, opening switch $S_1$, momentarily closing switch $S_2$, etc. To discharge the load, the supply voltages, $V_{N-1}$ through $V_1$ are switched in reverse order. Switch 684 is then closed, connecting the output to ground.

If N steps are used, the dissipation energy per step is calculated using the following formula:

$$E_{step} = \tfrac{1}{2} C_L V^2$$

where $C_L$ is the capacitance at capacitor 682 and V is the supplied voltage. The dissipation energy is calculated in joules. To charge capacitor 682 all the way to supply voltage V, N steps are used. A full charge-discharge cycle will result twice the dissipation energy of the charging only. Thus, according to this analysis, charging by several steps reduces the dissipation energy per charge-discharge cycle, and thereby the total power dissipation, by a factor of N.

Figure 14A:
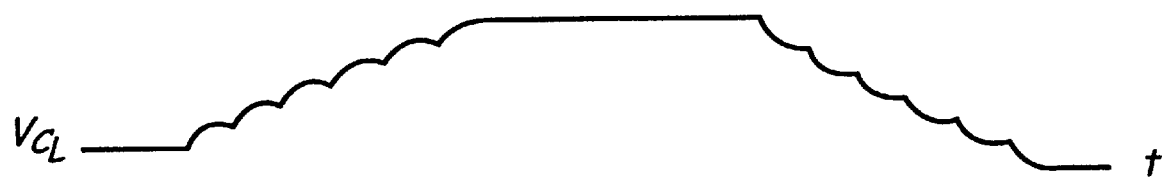
FIGS. 14A and 14B are graphs representing voltage versus time for various embodiments of the present invention.

FIG. 14A is a timing diagram illustrating voltage versus time at capacitor 682 shown in FIG. 13. As shown in FIG. 14A, the voltage at capacitor 682 is gradually ramped up from zero volts to supply voltage V. Similarly, the voltage is then ramped down from supply voltage V to zero volts. With the transition of ramped logic signal 686 from low to high and high to low in a gradual manner, minimal energy is released in the form of dissipated power during a switching operation.

Figure 14B:
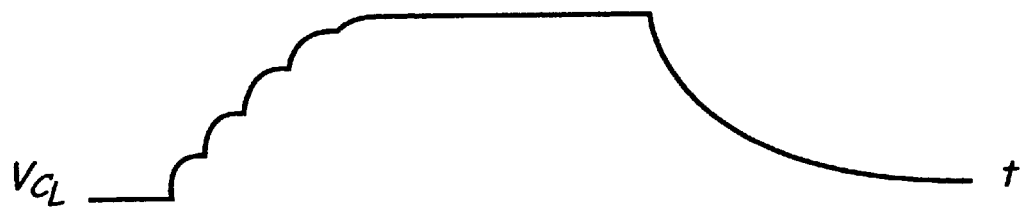

Alternatively, circuit 680, shown in FIG. 13, produces a similar but different timing diagram from that shown in FIG. 14A. In one embodiment, capacitor 682 is charged from zero volts to supply voltage V in the same manner as previously discussed. However, in order to provide a discharge portion of the cycle, switch 684 is closed, which discharges the voltage at capacitor 682. An exponential discharge effect is produced for capacitor 682. The timing diagram for this alternative scenario is shown in FIG. 14B. It should be noted that this exemplary embodiment assumes a smaller, higher resistance switch 684 than the previous examples.

Figure 15:
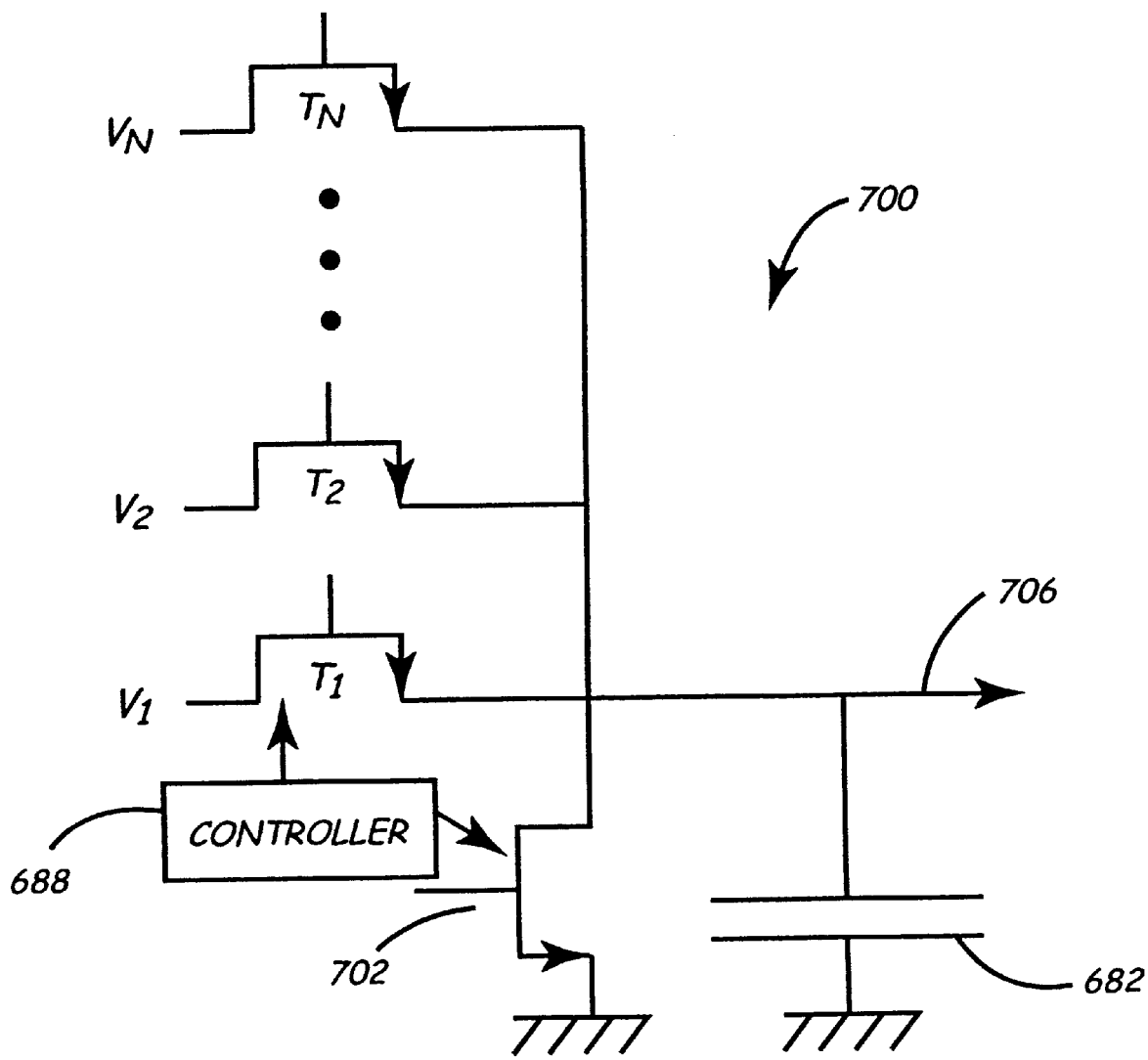
FIG. 15 is a circuit diagram illustrating the embodiment of the present invention shown in FIG. 13 including numerous transistors.

FIG. 15 is a schematic diagram illustrating the embodiment of the invention shown in FIG. 13 including numerous transistors. Circuitry 700 is similar to circuitry 680 shown in FIG. 13, with the exception of transistors $T_1$–$T_N$ replacing switches $S_1$–$S_N$. In one preferred embodiment, transistors $T_1$–$T_N$ are either N channel or P channel CMOS devices. Circuitry 700 operates similar to circuitry 680 shown in FIG. 13. For example, circuitry 700 provides ramped logic signal 706 to circuitry within implantable medical device 600. Further, in one preferred embodiment, circuitry 700 operates at a frequency of less than 500 kilohertz. Further, supply voltages $V_1$–$V_N$ are evenly distributed between ground and $V_N$ so that the voltage difference between any two adjacent supplies is the same. Each of the voltages is selectively applied to capacitor 682 by N transistors including first transistor $T_1$ and N-1 additional transistors. As in the previous circuit, transistors $T_1$–$T_N$ and transistor 702 are controlled by controller 688. Transistor 702 can be used to set an initial, known condition on capacitor 682. To charge the capacitor 682, transistor 702 is open and supply voltages $V_1$–$V_N$ are connected to capacitor 682 in succession by selectively turning on the transistors, that is, by momentarily closing transistor $T_1$, opening transistor $T_1$, momentarily closing transistor $T_2$, etc. To discharge the load, the supply voltages $V_1$–$V_N$ are applied to the load in reverse order. Transistor 702 is then closed, connecting the output to ground. The above-discussed sequence would produce a timing diagram such as illustrated in FIG. 14A.

As with circuitry 680 shown in FIG. 13, circuitry 700 shown in FIG. 15 alternatively produces a similar but different timing diagram from that shown in FIG. 14A. For example, capacitor 682 can be charged from zero volts to supply voltage V in the same manner as previously discussed. However, in order to provide a discharge portion of the cycle, transistors $T_1$–$T_N$ are opened and transistor 702 is closed, thereby creating a resistive path to ground. An exponential discharge effect is produced for capacitor 682. The timing diagram for this alternative scenario is shown in FIG. 14B.

Figure 16:
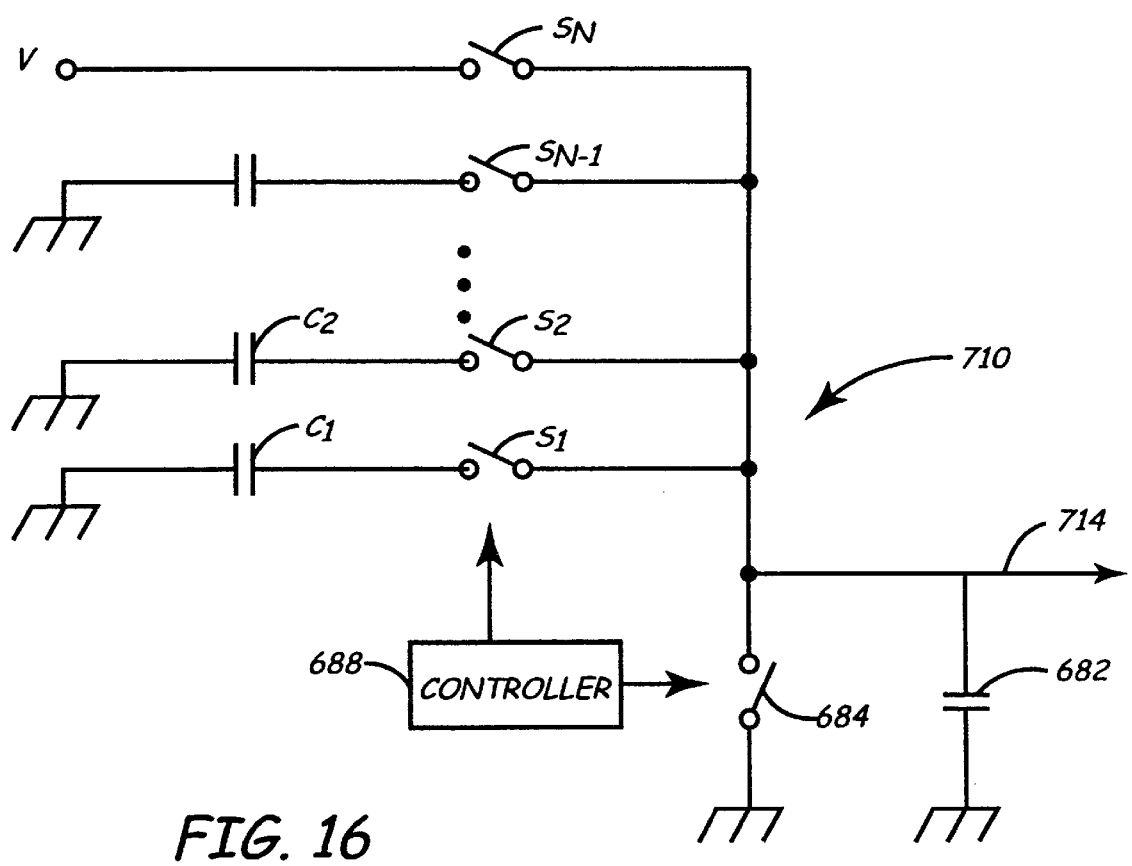
FIG. 16 is a circuit diagram illustrating another embodiment of the present invention utilizing adiabatic logic within the implantable medical device.

Circuitry 710, shown in FIG. 16 discloses another embodiment of the present invention that utilizes adiabatic logic to minimize power consumption within an implantable medical device. Circuitry 710 provides ramped logic signal 714 to circuitry within implantable medical device 600. Circuitry 710, is similar to circuitry 680 shown in FIG. 13, operating at a frequency of less than 500 kilohertz. However, capacitors $C_1$–$C_{N-1}$ replaces voltage sources $V_1$–$V_{N-1}$ connected between ground and switches $S_1$–$S_{N-1}$, respectively. In one preferred embodiment, capacitors $C_1$–$C_{N-1}$ are tank capacitors with a capacitance much larger (e.g., in order of magnitude) than capacitor 682. Once again, in one preferred embodiment, capacitor 682 represents an internal capacitance comprising the total capacitance of the internal nodes connected to a bus. In one preferred embodiment, capacitors $C_1$–$C_{N-1}$ have identical values to produce a symmetrical logic signal 714.

Figure 17:
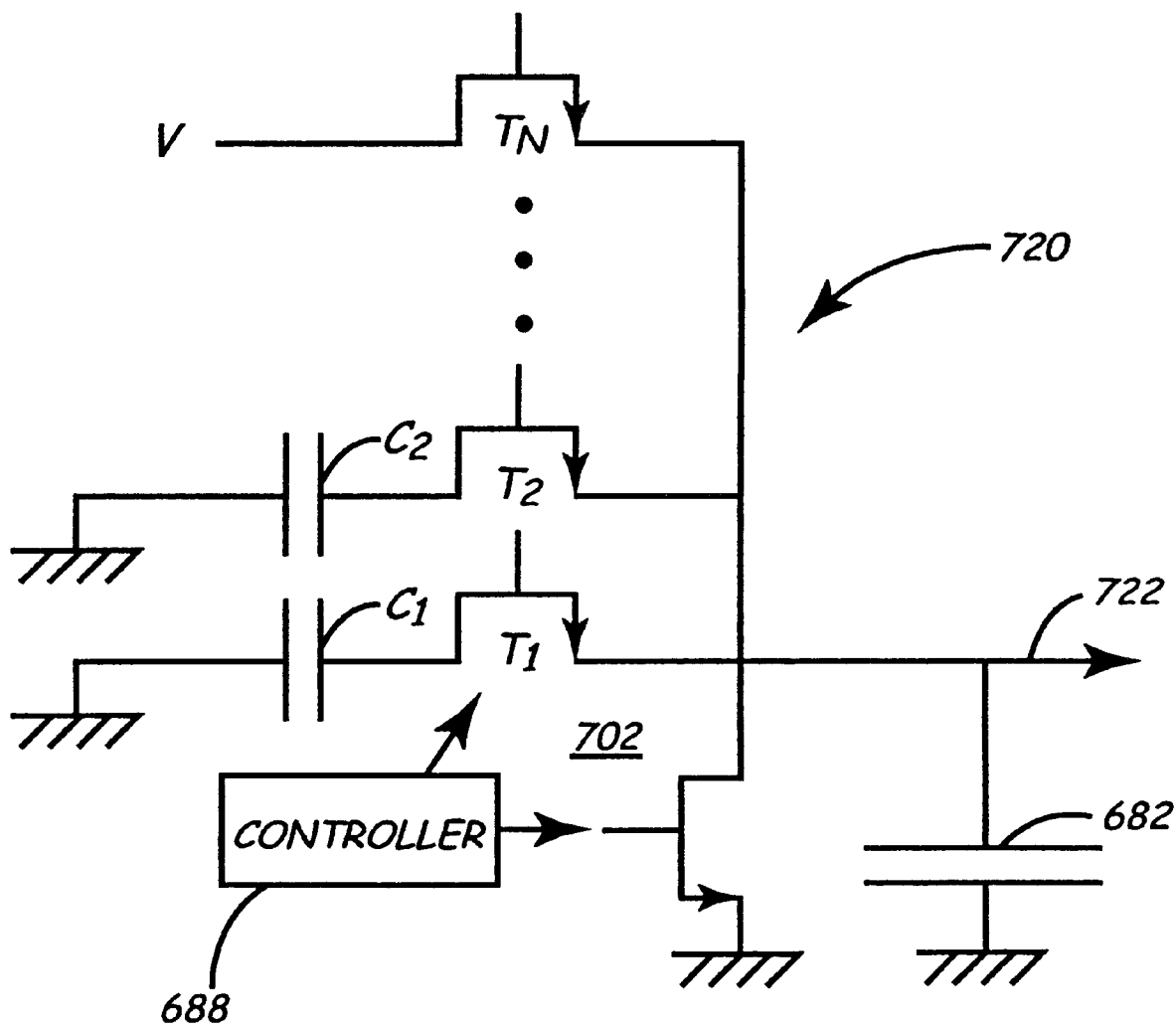
FIG. 17 is a circuit diagram illustrating the embodiment of the present invention shown in FIG. 16 including numerous transistors.
Figure 18:
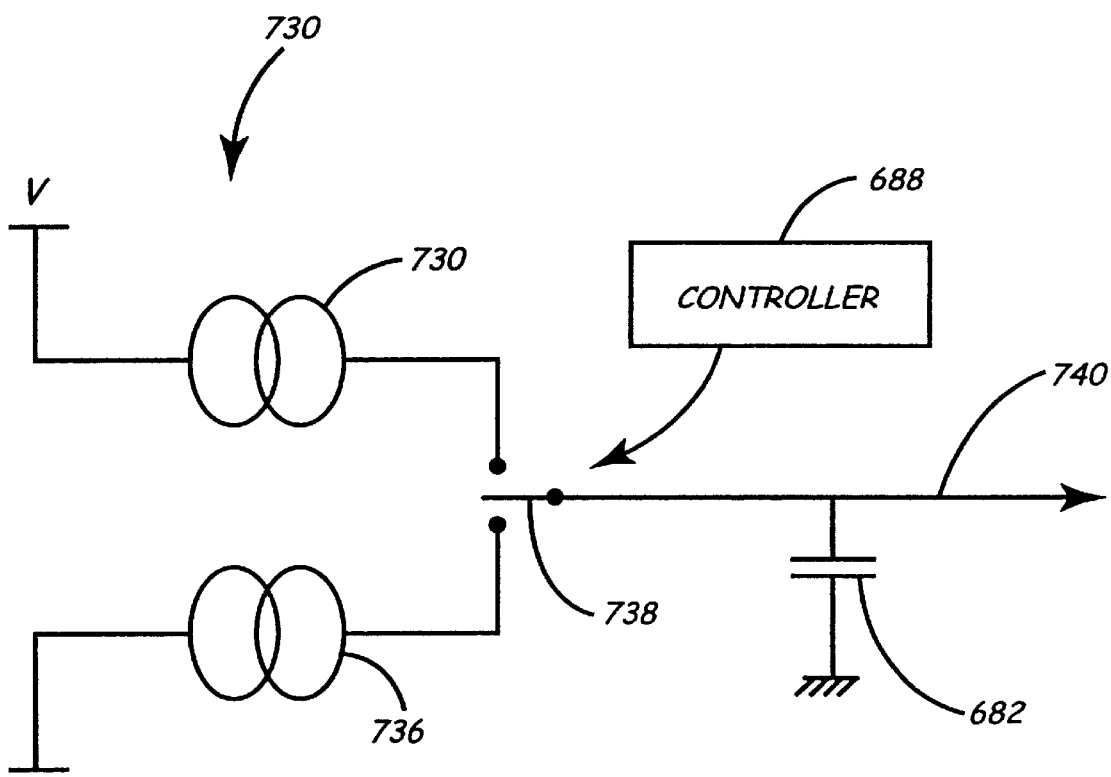
FIG. 18 is a circuit diagram illustrating yet another embodiment of the present invention utilizing adiabatic logic within the implantable medical device.

Circuitry 720, shown in FIG. 17, is similar to circuitry 710, shown in FIG. 16, with the exception that transistors $T_1$–$T_N$ replace switches $S_1$–$S_N$. As previously discussed, capacitors $C_1$–$C_{N-1}$ can be tank capacitors and transistors $T_1$–$T_N$ and 702 can be controlled by control 704. In one preferred embodiment, transistors $T_1$–$T_N$ can be either N channel or P channel devices. Circuitry 720 provides ramped logic signal 722 to circuitry within implantable medical device 600.

The embodiments shown in FIGS. 16 and 17 produce a similar logic signal to that shown in FIGS. 14A and 14B. Depending upon the operation of the circuitry, both circuits produce either a step-up and step-down ramp logic signal or produce a step-up and exponential down logic signal. In either case, the use of adiabatic logic reduces power dissipation during a switching operation.

Figure 19:
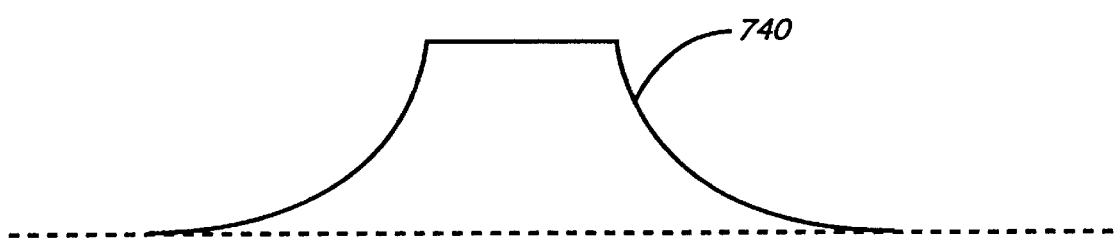
FIG. 19 is a graph representing voltage versus time for the circuit shown in FIG. 18.

FIG. 18 discloses yet another embodiment of the present invention. Circuitry 730, shown in FIG. 18, provides exponential logic signal 740 to circuitry within implantable medical device 600. Once again, capacitor 682 represents an internal capacitance comprising the total capacitance of the internal nodes connected to a bus, such as buses 626A–626F, 638, and 660. Circuitry 730 also includes voltage source V, current sources 734 and 736, and switch 738. Current source 734 is connected between voltage source V and switch 738, while current source 736 is connected between switch 738 and ground. The position of switch 738 determines whether capacitor 682 is charging or discharging. Due to the charging and discharging capabilities of capacitor 682, circuitry 730 will produce exponential logic signal 740 as shown in FIG. 19. As can be seen in FIG. 19, circuitry 730 produces an exponentially increasing first portion of exponential logic signal 740, while also producing an exponentially decreasing second portion of exponential logic signal 740. In one preferred embodiment, current source 734 and 736 would have identical values, such as in the range of 10–1000 pA.

FIG. 20 is yet another embodiment which discloses an adiabatic logic system which minimizes power dissipation of a continuously switching clock signal. While the embodiment shown in FIGS. 13 and 15–18 are used in conjunction with a bus within implantable medical device 600, circuitry 750, shown in FIG. 20, is used within implantable medical device 600 in conjunction with a clock signal. For example, circuitry 750, shown in FIG. 20, can be used within clocks 614 or 632, or in conjunction with timers 616 or 634 shown in FIG. 20. As shown in FIG. 20, circuitry 750 includes buffer circuit 752, inductor 754, and inverter circuit 756. Buffer circuit 752 further includes transistors 758 and 760, voltage sources $V_{DD}$ and $V_{SS}$, and resistor 762, which represents an output resistance of buffer 752. Inverter circuit 756 further comprises inverter element 764 and capacitor 766, which represents an internal nodal input capacitance of inverter circuit 756.

FIG. 20 represents circuit 750. The major segments of circuit 750 include inductor 754 in series with buffer circuit 752 and inverter circuit 756. Buffer circuit 752 includes transistors 758 and 760 set across voltage sources $V_{DD}$ and $V_{SS}$. The transistors are in series with resistor 762, which is in turn serially connected to inductor 754. Similarly, inverter circuit 756 includes inverter element 764 connected in series with inductor 754. Capacitor 766 represents an internal capacitance between an input of inventor element 764 and ground.

Circuitry 750, shown in FIG. 20, utilizes one-half of the energy to power an equivalent logic circuit used in a standard clock signal compared to a prior art design. Buffer 752 via large P-type transistor 758 produces a fast rising edge of a standard square wave. The falling edge output of buffer 752 is produced by a much smaller N-type transistor 760. This pairing of large, P-type transistor 758 and small, N-type transistor 760 substantially decreases the crowbar current in buffer 752. The falling or trailing edge of logic signal 768 is produced by allowing circuitry 750 to simply ring with the negative cycle. Thus, circuitry 750 reduces the power consumption of a standard circuit by one-half, while enabling generation of logic signal 768 for transmission to a sub-component of implantable medical device 600.

The present invention is compatible with various fabrication technologies such as silicon on insulator (SOI), silicon on sapphire (SOS) CMOS technologies as well as conventional silicon CMOS technologies. In one embodiment of the invention, adiabatic logic permits more functions to be performed by the DSPs due to the reduced power dissipation. Further, multiple processor based designs may also be implemented including adiabatic logic to reduce power dissipation as supply voltages and clocking frequencies are reduced for various functions performed by the processors.

In addition, as the power consumption is reduced by incorporating adiabatic logic of the invention into devices, further functionality can be added to the devices, thus taking advantage of the power conservation aspects of the present invention. For example, morphology detection functions may be added without increasing energy dissipation. Specifically, differentiation of retrograde P-waves and antegrade P-waves of EGM waveform; differentiation of P-waves from far field R-waves; differentiation of AF-A flutter-AT from sinus tachycardia; differentiation of VT-VF-V flutter from SVT; and differentiation of cardiac signals from electromagnetic interference may be implemented using the detection circuits of the present invention.

The preceding specific embodiments are illustrative of the practice of the invention. It is to be understood, therefore, that other expedients known to those skilled in the art or disclosed herein may be employed without departing from the invention or the scope of the appended claims. For example, the present invention is not limited to the use of clock source providing discrete clock frequencies, but such clock frequencies may be varied in a continuous manner. Further, the supply voltage source may include not only discrete supply voltages, but may be a voltage source that is varied continuously over a particular voltage range such as with a voltage regulator. The present invention is also not limited to use in conjunction with pacemakers or PCDs, but may find further application in other relevant areas such as telecommunications where low power consumption is desired. The present invention further includes within its scope methods of making and using the just-in-time clocking and/or multiple supply voltage concepts described herein above.

In the claims, mean plus function clauses are intended to cover the structures described herein as performing the recited function and not only structural equivalents but also equivalent structures. Thus, although a nail and a screw may not be structural equivalents in that a nail employs a cylindrical surface to secure wooden parts together, whereas a screw employs a helical surface, in the environment of fastening wooden parts a nail and a screw are equivalent structures.

What is claimed is:

1. An implantable medical device system having a bus and first and second logic electrical components, said bus extending between said components, said system for generating a logic signal and for minimizing power dissipation within the implantable medical device, the system comprising:

means for defining a first potential;

a capacitive element associated with the bus and the first potential;

N voltage supplies, wherein N>1;

N switches corresponding to the N voltage supplies, each switch being operatively coupled between a corresponding one of the N voltage supplies and the capacitive element;

a first switch operatively coupled in parallel with the capacitive element between the N switches and the first potential; and a controller operatively coupled to the N switches and to the first switch to control the N switches to generate a ramped logic signal across the capacitive element that is applied to the bus and to either logic electrical component and to control the first switch to reset the voltage on the capacitor to the first potential.

2. The system of claim 1, wherein the capacitive element includes an internal capacitance within the bus between the first electrical component and the second electrical component of the implantable medical device.

3. The system of claim 2, wherein the logic signal generated across the capacitive element is provided to the first electrical component.

4. The system of claim 2, wherein the logic signal generated across the capacitive element is provided to the second electrical component.

5. The system of claim 1, wherein the logic signal generated across the capacitive element operates at a frequency of less than 500 kilohertz.

6. The system of claim 1, wherein the controller is operable to open the first switch and to selectively close the N switches in a timed sequence to charge the capacitive element from the first potential through N voltage steps, thereby providing a ramped leading edge of the logic signal.

7. The system of claim 6, wherein the controller is operable to selectively open the N switches in a timed sequence and to close the first switch after all of the N switches are opened to discharge the capacitive element to the first potential, thereby providing a ramped trailing edge of the logic signal.

* * * * *